(12) United States Patent
Duchon et al.

(10) Patent No.: US 7,901,363 B2
(45) Date of Patent: Mar. 8, 2011

(54) BODY FLUID SAMPLING DEVICE AND METHODS OF USE

(75) Inventors: Brent G. Duchon, Cypress, CA (US);
Joel S. Douglas, Groton, CT (US);
Jeffrey N. Roe, San Ramon, CA (US);
Ryszard Radwanski, Lublin (PL);
Andrew M. Drexler, Los Altos Hills, CA (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1519 days.

(21) Appl. No.: 10/753,973

(22) Filed: Jan. 8, 2004

(65) Prior Publication Data
US 2004/0162506 A1 Aug. 19, 2004

Related U.S. Application Data

(63) Continuation of application No. 10/128,780, filed on Apr. 23, 2002, now Pat. No. 7,235,056, which is a continuation of application No. 09/528,097, filed on Mar. 17, 2000, now abandoned, which is a continuation of application No. 09/204,909, filed on Dec. 3, 1998, now Pat. No. 6,056,701, which is a continuation of application No. 08/857,680, filed on May 16, 1997, now Pat. No. 5,879,311.

(60) Provisional application No. 60/017,133, filed on May 17, 1996, provisional application No. 60/019,918, filed on Jun. 14, 1996, provisional application No. 60/023,658, filed on Aug. 1, 1996, provisional application No. 60/025,340, filed on Sep. 3, 1996, provisional application No. 60/092,121, filed on Sep. 16, 1996.

(51) Int. Cl.
*A61B 5/00* (2006.01)

(52) U.S. Cl. .......................................... 600/583; 606/181
(58) Field of Classification Search .................. 600/583; 606/181
See application file for complete search history.

(56) References Cited

U.S. PATENT DOCUMENTS 720,906 A 2/1903 Eilrich et al.
(Continued)

FOREIGN PATENT DOCUMENTS

DE 1 938 870 1/1970
(Continued)

OTHER PUBLICATIONS

Ash et al., "Subcutaneous Capillary Filtrate Collector for Measurement of Blood Glucose", ASAIO Journal, 1992.
(Continued)

*Primary Examiner* — Max Hindenburg
*Assistant Examiner* — Renee Danega
(74) *Attorney, Agent, or Firm* — Woodard, Emhardt, Moriarty, McNett & Henry LLP

(57) ABSTRACT

A device for sampling body fluid includes a housing having a sleeve at a forward end thereof which is displaceable in response to being pressed against a user's skin to trigger the firing of a lancet. After the lancet is removed from the incision, the sleeve is repeatedly pressed against the skin to depress a ring of body tissue in surrounding relationship to the incision to express body fluid outwardly through the incision. A pusher member is then actuated to push a capillary tube through a front end of the housing for drawing-in body fluid. The lancet is a disposable lancet which includes a body supporting a skin-lancing member and the capillary tube. The disposable lancet passes through an upper end of a lancet carrier when being installed or removed. The device cannot be armed until the disposable lancet is installed in the housing, because the capillary tube functions to push a safety device to a non-safety position.

14 Claims, 11 Drawing Sheets

U.S. PATENT DOCUMENTS

| | | | |
|---|---|---|---|
| 1,960,889 A | 5/1934 | Benedict | |
| 2,594,621 A | 4/1952 | Derrick | |
| 2,848,799 A | 7/1953 | Jacoby | |
| 2,714,890 A | 8/1955 | Vang | |
| 3,030,959 A | 4/1962 | Grunert | |
| 3,040,744 A | 6/1962 | Hoggard | |
| 3,068,868 A | 12/1962 | Skopyk | |
| 3,086,288 A | 4/1963 | Balamuth et al. | |
| 3,208,452 A | 9/1965 | Stern | |
| 3,221,739 A | 12/1965 | Rosenthal | |
| 3,235,337 A | 2/1966 | Artis | |
| 3,358,689 A | 12/1967 | Higgins | |
| 3,486,504 A | 12/1969 | Austin | |
| 3,623,475 A | 11/1971 | Sanz | |
| 3,626,929 A | 12/1971 | Sanz et al. | |
| 3,640,267 A | 2/1972 | Hurtig et al. | |
| 3,673,475 A | 6/1972 | Britton, Jr. | |
| 3,685,509 A | 8/1972 | Bentall | |
| 3,734,085 A | 5/1973 | Russell | |
| 3,741,197 A | 6/1973 | Sanz et al. | |
| 3,774,611 A | 11/1973 | Tussey et al. | |
| 3,832,776 A | 9/1974 | Sawyer | |
| 3,933,439 A | 1/1976 | McDonald | |
| D238,710 S | 2/1976 | Cacanindin | |
| 3,964,482 A | 6/1976 | Gerstel et al. | |
| 4,077,406 A | 3/1978 | Sandhage et al. | |
| 4,151,832 A | 5/1979 | Hamer | |
| 4,154,228 A | 5/1979 | Feldstein et al. | |
| D254,444 S | 3/1980 | Levine | |
| 4,203,446 A | 5/1980 | Hofert et al. | |
| 4,222,380 A | 9/1980 | Terayama | |
| 4,223,674 A | 9/1980 | Fluent et al. | |
| 4,230,118 A | 10/1980 | Holman et al. | |
| 4,235,234 A | 11/1980 | Whitney et al. | |
| 4,356,826 A | 11/1982 | Kubota | |
| 4,360,016 A * | 11/1982 | Sarrine | 600/576 |
| 4,368,738 A | 1/1983 | Tersteegen et al. | |
| 4,375,815 A | 3/1983 | Burns | |
| 4,383,530 A | 5/1983 | Bruno | |
| 4,397,643 A | 8/1983 | Rygiel | |
| 4,441,510 A * | 4/1984 | Worley et al. | 600/576 |
| 4,449,529 A | 5/1984 | Burns et al. | |
| 4,460,354 A | 7/1984 | Weilbacher et al. | |
| 4,462,405 A | 7/1984 | Erhlich | |
| 4,469,110 A | 9/1984 | Slama | |
| 4,503,856 A | 3/1985 | Cornell et al. | |
| 4,517,978 A | 5/1985 | Levin et al. | |
| 4,518,384 A | 5/1985 | Tarello et al. | |
| 4,535,773 A | 8/1985 | Yoon | |
| 4,553,541 A * | 11/1985 | Burns | 606/182 |
| 4,562,842 A | 1/1986 | Morfeld et al. | |
| 4,564,513 A | 1/1986 | Becher et al. | |
| 4,577,630 A * | 3/1986 | Nitzsche et al. | 606/182 |
| 4,580,564 A | 4/1986 | Anderson | |
| 4,622,974 A | 11/1986 | Coleman et al. | |
| 4,627,445 A | 12/1986 | Garcia et al. | |
| 4,637,403 A | 1/1987 | Garcia et al. | |
| 4,637,978 A | 1/1987 | Dappen | |
| 4,648,408 A | 3/1987 | Hutcheson et al. | |
| 4,653,511 A | 3/1987 | Goch | |
| 4,653,513 A | 3/1987 | Dombrowski | |
| 4,658,821 A | 4/1987 | Chiodo et al. | |
| 4,660,570 A | 4/1987 | Dombrowski | |
| 4,677,979 A | 7/1987 | Burns | |
| 4,685,463 A | 8/1987 | Williams | |
| 4,687,000 A | 8/1987 | Eisenhardt et al. | |
| 4,750,489 A | 6/1988 | Berkman et al. | |
| 4,772,264 A * | 9/1988 | Cragg | 604/158 |
| 4,787,398 A * | 11/1988 | Garcia et al. | 600/583 |
| 4,790,979 A | 12/1988 | Terminiello et al. | |
| 4,794,926 A | 1/1989 | Munsch et al. | |
| 4,805,623 A | 2/1989 | Jobsis | |
| 4,823,806 A | 4/1989 | Bajada | |
| RE32,922 E | 5/1989 | Levin et al. | |
| 4,837,049 A | 6/1989 | Byers et al. | |
| 4,844,095 A | 7/1989 | Chiodo et al. | |
| 4,850,973 A | 7/1989 | Jordan et al. | |
| 4,858,607 A | 8/1989 | Jordan et al. | |
| 4,869,249 A | 9/1989 | Crossman et al. | |
| 4,873,993 A | 10/1989 | Meserol et al. | |
| 4,883,068 A | 11/1989 | Dechow | |
| D305,065 S | 12/1989 | Büchel et al. | |
| 4,895,147 A | 1/1990 | Bodicky et al. | |
| 4,920,977 A | 5/1990 | Haynes | |
| 4,924,879 A * | 5/1990 | O'Brien | 600/583 |
| 4,925,447 A | 5/1990 | Rosenblatt | |
| 4,953,552 A | 9/1990 | DeMarzo | |
| 4,976,724 A | 12/1990 | Nieto et al. | |
| 4,981,473 A | 1/1991 | Rosenblatt | |
| 4,983,178 A | 1/1991 | Schnell | |
| 4,990,154 A | 2/1991 | Brown et al. | |
| 4,994,068 A | 2/1991 | Hufnagle | |
| 4,994,073 A | 2/1991 | Green | |
| 4,994,079 A | 2/1991 | Genese et al. | |
| 4,995,402 A | 2/1991 | Smith et al. | |
| 5,002,054 A | 3/1991 | Ash et al. | |
| 5,014,718 A | 5/1991 | Mitchen | |
| 5,019,059 A | 5/1991 | Goldberg et al. | |
| 5,029,583 A | 7/1991 | Meserol et al. | |
| 5,035,704 A | 7/1991 | Lambert et al. | |
| 5,047,044 A | 9/1991 | Smith et al. | |
| 5,052,403 A | 10/1991 | Haber et al. | |
| 5,054,499 A | 10/1991 | Swierczek | |
| 5,066,859 A | 11/1991 | Karkar et al. | |
| 5,070,884 A | 12/1991 | Columbus et al. | |
| 5,070,886 A | 12/1991 | Mitchen et al. | |
| D324,423 S | 3/1992 | Ahlstrand et al. | |
| 5,097,810 A | 3/1992 | Fishman et al. | |
| 5,100,620 A | 3/1992 | Brenneman | |
| 5,102,404 A | 4/1992 | Goldberg et al. | |
| 5,108,889 A | 4/1992 | Smith | |
| 5,145,565 A | 9/1992 | Kater et al. | |
| 5,152,775 A | 10/1992 | Ruppert | |
| 5,163,442 A | 11/1992 | Ono | |
| 5,165,418 A | 11/1992 | Tankovich | |
| D332,306 S | 1/1993 | Garth et al. | |
| 5,188,118 A * | 2/1993 | Terwilliger | 600/566 |
| 5,189,751 A | 3/1993 | Giuliani et al. | |
| 5,193,552 A | 3/1993 | Columbus et al. | |
| 5,195,534 A | 3/1993 | Sarrine | |
| 5,201,324 A | 4/1993 | Swierczek | |
| 5,212,879 A | 5/1993 | Biro et al. | |
| 5,217,480 A | 6/1993 | Haber et al. | |
| 5,222,504 A | 6/1993 | Solomon | |
| 5,231,993 A | 8/1993 | Haber et al. | |
| 5,269,800 A | 12/1993 | Davis, Jr. | |
| 5,271,385 A | 12/1993 | Bailey | |
| 5,277,198 A | 1/1994 | Kanner et al. | |
| 5,279,294 A * | 1/1994 | Anderson et al. | 600/322 |
| 5,279,586 A | 1/1994 | Balkwill | |
| 5,282,822 A | 2/1994 | Macors et al. | |
| 5,290,420 A | 3/1994 | Matson | |
| 5,304,193 A | 4/1994 | Zhadanov | |
| 5,309,924 A | 5/1994 | Peabody | |
| 5,314,441 A | 5/1994 | Cusack et al. | |
| 5,314,442 A | 5/1994 | Morita | |
| 5,318,583 A | 6/1994 | Rabenau et al. | |
| 5,318,584 A | 6/1994 | Lange et al. | |
| 5,320,607 A * | 6/1994 | Ishibashi | 604/115 |
| 5,320,808 A | 6/1994 | Holen et al. | |
| 5,324,302 A | 6/1994 | Crouse | |
| 5,324,303 A | 6/1994 | Strong et al. | |
| 5,353,806 A | 10/1994 | Heinzelman et al. | |
| 5,366,470 A | 11/1994 | Ramel | |
| 5,368,047 A | 11/1994 | Suzuki et al. | |
| 5,387,203 A | 2/1995 | Goodrich | |
| 5,395,387 A | 3/1995 | Burns | |
| 5,402,798 A | 4/1995 | Swierczek et al. | |
| 5,415,169 A | 5/1995 | Siczek et al. | |
| 5,421,816 A | 6/1995 | Lipkovker | |
| 5,423,758 A | 6/1995 | Shaw | |
| 5,423,847 A | 6/1995 | Strong et al. | |
| 5,437,640 A | 8/1995 | Schwab | |
| 5,439,473 A | 8/1995 | Jorgensen | |
| 5,445,611 A | 8/1995 | Eppstein et al. | |
| 5,456,875 A | 10/1995 | Lambert | |
| 5,458,140 A | 10/1995 | Eppstein et al. | |

| | | | | | |
|---|---|---|---|---|---|
| 5,472,427 A | 12/1995 | Rammler | 5,935,864 A | 8/1999 | Schramm et al. |
| 5,474,084 A | 12/1995 | Cunniff | 5,938,679 A | 8/1999 | Freeman et al. |
| 5,476,474 A | 12/1995 | Davis et al. | 5,947,957 A | 9/1999 | Morris |
| 5,487,748 A | 1/1996 | Marshall et al. | 5,948,695 A | 9/1999 | Douglas et al. |
| 5,510,266 A | 4/1996 | Bonner et al. | 5,951,492 A | 9/1999 | Douglas et al. |
| 5,512,158 A | 4/1996 | Cole | 5,951,493 A | 9/1999 | Douglas et al. |
| 5,514,152 A | 5/1996 | Smith | 5,951,582 A | 9/1999 | Thorne et al. |
| 5,518,006 A | 5/1996 | Mawhirt et al. | 5,964,718 A | 10/1999 | Duchon et al. |
| 5,529,074 A | 6/1996 | Greenfield | 5,968,063 A | 10/1999 | Chu et al. |
| 5,529,581 A | 6/1996 | Cusack | 5,971,941 A | 10/1999 | Simons et al. |
| D371,440 S | 7/1996 | Petersen | 5,984,940 A | 11/1999 | Davis et al. |
| 5,540,709 A | 7/1996 | Ramel | 5,997,561 A | 12/1999 | Bocker et al. |
| 5,545,173 A | 8/1996 | Herbst | 6,015,392 A | 1/2000 | Douglas et al. |
| 5,545,174 A | 8/1996 | Schenk et al. | 6,022,324 A | 2/2000 | Skinner |
| 5,549,584 A | 8/1996 | Gross | 6,022,366 A | 2/2000 | Schraga |
| 5,554,166 A * | 9/1996 | Lange et al. ............. 606/182 | 6,027,459 A | 2/2000 | Shain et al. |
| 5,569,212 A | 10/1996 | Brown | 6,036,924 A | 3/2000 | Simons et al. |
| 5,575,403 A | 11/1996 | Charlton et al. | 6,045,567 A | 4/2000 | Taylor et al. |
| 5,582,184 A | 12/1996 | Erickson et al. | 6,048,352 A | 4/2000 | Douglas et al. |
| 5,591,139 A | 1/1997 | Lin et al. | 6,056,701 A | 5/2000 | Duchon et al. |
| D378,612 S | 3/1997 | Clark et al. | 6,056,765 A | 5/2000 | Bajaj et al. |
| 5,607,401 A | 3/1997 | Humphrey | 6,063,039 A | 5/2000 | Cunningham et al. |
| 5,611,809 A | 3/1997 | Marshall et al. | 6,066,103 A | 5/2000 | Duchon et al. |
| 5,613,978 A | 3/1997 | Harding | 6,068,599 A | 5/2000 | Saito et al. |
| 5,624,458 A | 4/1997 | Lipscher | 6,071,249 A | 6/2000 | Cunningham et al. |
| 5,628,309 A | 5/1997 | Brown | 6,071,250 A | 6/2000 | Douglas et al. |
| 5,628,764 A | 5/1997 | Schraga | 6,071,251 A | 6/2000 | Cunningham et al. |
| 5,628,765 A | 5/1997 | Morita | 6,071,294 A | 6/2000 | Simons et al. |
| 5,630,986 A | 5/1997 | Charlton et al. | 6,080,116 A | 6/2000 | Erickson et al. |
| 5,632,410 A | 5/1997 | Moulton et al. | 6,086,545 A | 7/2000 | Roe et al. |
| 5,636,640 A | 6/1997 | Staehlin | 6,090,078 A | 7/2000 | Erskine |
| 5,638,828 A | 6/1997 | Lauks et al. | 6,093,156 A | 7/2000 | Cunningham et al. |
| 5,662,127 A | 9/1997 | De Vaughn | 6,099,484 A | 8/2000 | Douglas et al. |
| 5,666,966 A | 9/1997 | Horie et al. | 6,117,630 A | 9/2000 | Reber et al. |
| 5,671,753 A | 9/1997 | Pitesky | 6,120,462 A | 9/2000 | Hibner et al. |
| 5,680,872 A | 10/1997 | Sesekura et al. | 6,120,676 A | 9/2000 | Heller et al. |
| 5,682,233 A | 10/1997 | Brinda | 6,132,449 A | 10/2000 | Lum et al. |
| 5,700,695 A * | 12/1997 | Yassinzadeh et al. ...... 436/180 | 6,136,013 A | 10/2000 | Marshall et al. |
| 5,707,384 A | 1/1998 | Kim | 6,139,562 A | 10/2000 | Mauze et al. |
| 5,709,699 A | 1/1998 | Warner | 6,143,164 A | 11/2000 | Heller et al. |
| 5,714,390 A | 2/1998 | Hallowitz et al. | 6,146,361 A | 11/2000 | DiBiasi et al. |
| 5,720,924 A | 2/1998 | Eikmeier et al. | 6,152,889 A | 11/2000 | Sopp et al. |
| 5,730,357 A | 3/1998 | Besenschek et al. | 6,152,942 A | 11/2000 | Brenneman et al. |
| 5,730,753 A | 3/1998 | Morita | 6,155,992 A | 12/2000 | Henning et al. |
| 5,738,244 A | 4/1998 | Charlton et al. | 6,156,050 A | 12/2000 | Davis et al. |
| 5,741,291 A | 4/1998 | Yoo | 6,156,051 A | 12/2000 | Schraga |
| RE35,803 E | 5/1998 | Lange et al. | 6,159,424 A | 12/2000 | Kauhaniemi et al. |
| 5,746,217 A | 5/1998 | Erickson et al. | 6,162,639 A | 12/2000 | Douglas |
| 5,755,733 A | 5/1998 | Morita | 6,171,325 B1 | 1/2001 | Mauze et al. |
| 5,757,666 A | 5/1998 | Schreiber et al. | 6,176,865 B1 | 1/2001 | Mauze et al. |
| 5,758,643 A | 6/1998 | Wong et al. | 6,183,434 B1 | 2/2001 | Eppstein |
| 5,776,157 A | 7/1998 | Thorne et al. | 6,183,489 B1 | 2/2001 | Douglas et al. |
| 5,788,651 A | 8/1998 | Weilandt | 6,193,673 B1 | 2/2001 | Viola et al. |
| 5,788,652 A | 8/1998 | Rahn | 6,203,504 B1 | 3/2001 | Latterell et al. |
| 5,800,781 A * | 9/1998 | Gavin et al. ............... 422/73 | 6,206,841 B1 | 3/2001 | Cunningham et al. |
| 5,801,057 A | 9/1998 | Smart et al. | 6,210,420 B1 | 4/2001 | Mauze et al. |
| 5,810,199 A | 9/1998 | Charlton et al. | 6,210,421 B1 | 4/2001 | Bocker et al. |
| 5,820,570 A | 10/1998 | Erickson et al. | 6,228,100 B1 | 5/2001 | Schraga |
| 5,823,973 A | 10/1998 | Racchini et al. | 6,231,531 B1 | 5/2001 | Lum et al. |
| 5,830,219 A | 11/1998 | Bird et al. | 6,261,241 B1 | 7/2001 | Burbank et al. |
| 5,846,490 A | 12/1998 | Yokota et al. | 6,261,244 B1 | 7/2001 | Kensey et al. |
| 5,851,215 A | 12/1998 | Mawhirt et al. | 6,261,245 B1 | 7/2001 | Kawai et al. |
| 5,854,074 A | 12/1998 | Charlton et al. | 6,271,045 B1 | 8/2001 | Douglas et al. |
| 5,855,801 A | 1/1999 | Lin et al. | 6,283,926 B1 | 9/2001 | Cunningham et al. |
| 5,857,983 A | 1/1999 | Douglas et al. | 6,283,982 B1 | 9/2001 | Levaughn et al. |
| 5,863,800 A | 1/1999 | Eikmeier et al. | 6,285,454 B1 | 9/2001 | Douglas et al. |
| 5,871,494 A | 2/1999 | Simons et al. | 6,306,104 B1 | 10/2001 | Cunningham et al. |
| 5,873,887 A | 2/1999 | King et al. | 6,306,152 B1 | 10/2001 | Verdonk et al. |
| 5,879,311 A | 3/1999 | Duchon et al. | 6,315,738 B1 | 11/2001 | Nishikawa et al. |
| 5,879,367 A | 3/1999 | Latterell et al. | 6,319,210 B1 | 11/2001 | Douglas et al. |
| 5,880,829 A | 3/1999 | Kauhaniemi et al. | 6,332,871 B1 | 12/2001 | Douglas et al. |
| 5,885,211 A | 3/1999 | Eppstein et al. | 6,346,114 B1 | 2/2002 | Schraga |
| 5,885,219 A | 3/1999 | Nightengale | 6,352,514 B1 | 3/2002 | Douglas et al. |
| 5,891,053 A | 4/1999 | Sesekura | 6,364,889 B1 | 4/2002 | Kheiri et al. |
| 5,902,279 A | 5/1999 | Powles et al. | 6,364,890 B1 | 4/2002 | Lum et al. |
| 5,916,222 A | 6/1999 | Iwasaki et al. | 6,375,627 B1 | 4/2002 | Mauze et al. |
| 5,916,229 A | 6/1999 | Evans | 6,379,317 B1 | 4/2002 | Kintzig et al. |
| 5,916,230 A | 6/1999 | Brenneman et al. | 6,379,969 B1 | 4/2002 | Mauze et al. |
| 5,935,075 A | 8/1999 | Casscells et al. | 6,391,005 B1 | 5/2002 | Lum et al. |

| | | | | | |
|---|---|---|---|---|---|
| 6,402,701 B1 | 6/2002 | Kaplan et al. | FR | 2 590 673 | 5/1987 |
| 6,402,704 B1 | 6/2002 | McMorrow | GB | 2 222 251 A | 2/1990 |
| 6,409,740 B1 | 6/2002 | Kuhr et al. | JP | H02-120655 A | 5/1990 |
| 6,419,661 B1 | 7/2002 | Kuhr et al. | JP | H02-170388 A | 7/1990 |
| 6,423,011 B1 | 7/2002 | Arulkumaran et al. | JP | 04194660 A1 | 11/1990 |
| 6,455,324 B1 | 9/2002 | Douglas | JP | H06-004150 A | 1/1994 |
| 6,461,496 B1 | 10/2002 | Feldman et al. | JP | 08000598 | 1/1996 |
| 6,464,649 B1 | 10/2002 | Duchon et al. | JP | 09-084781 | 3/1997 |
| 6,472,220 B1 | 10/2002 | Simons et al. | JP | H09-089885 A | 4/1997 |
| 6,485,439 B1 | 11/2002 | Roe et al. | JP | 9-276235 | 10/1997 |
| 6,488,891 B2 | 12/2002 | Mason et al. | JP | H09-294737 | 11/1997 |
| 6,491,709 B2 | 12/2002 | Sharma et al. | JP | H11-164825 A | 6/1999 |
| 6,497,845 B1 | 12/2002 | Sacherer | JP | 2000116768 A2 | 4/2000 |
| 6,503,210 B1 | 1/2003 | Hirao et al. | JP | 2000-152923 A | 6/2000 |
| 6,506,575 B1 | 1/2003 | Knappe et al. | JP | 2001-095787 A | 4/2001 |
| 6,530,892 B1 | 3/2003 | Kelly | WO | WO 85/04089 A1 | 9/1985 |
| 6,589,260 B1 | 7/2003 | Schmelzeisen-Redeker et al. | WO | WO 88/00812 A1 | 2/1988 |
| 6,706,000 B2 | 3/2004 | Perez et al. | WO | WO 91/06855 A1 | 5/1991 |
| 6,706,159 B2 | 3/2004 | Moerman et al. | WO | WO 93/02720 A1 | 2/1993 |
| 6,730,046 B1 | 5/2004 | Hamamoto et al. | WO | WO 93/09723 | 5/1993 |
| 6,743,211 B1 | 6/2004 | Prausnitz et al. | WO | WO 93/12726 | 7/1993 |
| 6,752,817 B2 | 6/2004 | Flora et al. | WO | WO 94/16737 A1 | 8/1994 |
| 6,808,499 B1 | 10/2004 | Churchill et al. | WO | WO 95/10223 A2 | 4/1995 |
| 6,837,858 B2 | 1/2005 | Cunningham et al. | WO | WO 96/32635 A1 | 10/1996 |
| 7,041,068 B2 | 5/2006 | Freeman et al. | WO | WO 97/08986 A1 | 3/1997 |
| 2001/0011157 A1 | 8/2001 | Latterell et al. | WO | WO 97/42882 A1 | 11/1997 |
| 2001/0027327 A1 | 10/2001 | Schraga | WO | WO 97/42885 A1 | 11/1997 |
| 2001/0031931 A1 | 10/2001 | Cunningham et al. | WO | WO 97/42886 A1 | 11/1997 |
| 2001/0039387 A1 | 11/2001 | Rutynowski et al. | WO | WO 97/42888 | 11/1997 |
| 2001/0044615 A1 | 11/2001 | Amano et al. | WO | WO 97/43962 A1 | 11/1997 |
| 2002/0002344 A1 | 1/2002 | Douglas et al. | WO | WO 99/26539 A1 | 6/1999 |
| 2002/0004196 A1 | 1/2002 | Whitson | WO | WO 99/44508 | 9/1999 |
| 2002/0022789 A1 | 2/2002 | Perez et al. | WO | WO 99/55232 A1 | 11/1999 |
| 2002/0029059 A1 | 3/2002 | Purcell | WO | WO 00/45708 A1 | 8/2000 |
| 2002/0040230 A1 | 4/2002 | Kuhr et al. | WO | WO 01/00090 A1 | 1/2001 |
| 2002/0052618 A1 | 5/2002 | Haar et al. | WO | WO 01/34029 A1 | 5/2001 |
| 2002/0077584 A1 | 6/2002 | Lin et al. | WO | WO 01/64105 A1 | 9/2001 |
| 2002/0082522 A1 | 6/2002 | Douglas et al. | WO | WO 01/66010 A1 | 9/2001 |
| 2002/0082543 A1 | 6/2002 | Park et al. | WO | WO 01/72220 A1 | 10/2001 |
| 2002/0087110 A1 | 7/2002 | Effenhauser et al. | WO | WO 01/89383 A2 | 11/2001 |
| 2002/0103499 A1 | 8/2002 | Perez et al. | WO | WO 02/08753 A2 | 1/2002 |
| 2002/0115967 A1 | 8/2002 | Svedman | WO | WO 02/056769 A1 | 7/2002 |
| 2002/0169470 A1 | 11/2002 | Kuhr et al. | WO | WO 03/088834 A1 | 10/2003 |
| 2002/0177761 A1 | 11/2002 | Orloff et al. | WO | WO 03/088835 A2 | 10/2003 |
| 2002/0177788 A1 | 11/2002 | Hodges et al. | | | |
| 2003/0069509 A1 | 4/2003 | Matzinger et al. | | | |
| 2003/0083685 A1 | 5/2003 | Freeman et al. | | | |
| 2003/0083686 A1 | 5/2003 | Freeman et al. | | | |
| 2003/0088191 A1 | 5/2003 | Freeman et al. | | | |
| 2003/0093093 A1 | 5/2003 | Modesitt et al. | | | |
| 2003/0191415 A1 | 10/2003 | Moerman et al. | | | |
| 2003/0199789 A1 | 10/2003 | Boecker et al. | | | |
| 2003/0199790 A1 | 10/2003 | Boecker et al. | | | |
| 2003/0199791 A1 | 10/2003 | Boecker et al. | | | |
| 2003/0199898 A1 | 10/2003 | Boecker et al. | | | |
| 2003/0199899 A1 | 10/2003 | Boecker et al. | | | |
| 2003/0199901 A1 | 10/2003 | Boecker et al. | | | |
| 2003/0199902 A1 | 10/2003 | Boecker et al. | | | |
| 2003/0199903 A1 | 10/2003 | Boecker et al. | | | |
| 2003/0199909 A1 | 10/2003 | Boecker et al. | | | |
| 2003/0199911 A1 | 10/2003 | Boecker et al. | | | |
| 2003/0208140 A1 | 11/2003 | Pugh | | | |
| 2003/0212424 A1 | 11/2003 | Briggs et al. | | | |
| 2003/0233112 A1 | 12/2003 | Alden et al. | | | |
| 2003/0233113 A1 | 12/2003 | Alden et al. | | | |
| 2006/0178690 A1 | 8/2006 | Freeman et al. | | | |

FOREIGN PATENT DOCUMENTS

| | | |
|---|---|---|
| DE | 34 26 090 A1 | 4/1985 |
| DE | 35 08 365 A1 | 8/1985 |
| DE | 37 08 031 A1 | 11/1987 |
| EP | 0 212 906 A2 | 3/1987 |
| EP | 0 365 196 A1 | 4/1990 |
| EP | 0 453 283 A1 | 10/1991 |
| EP | 0 568 024 A2 | 11/1993 |
| EP | 0 671 146 A1 | 9/1995 |
| EP | 0 688 532 B1 | 12/1995 |
| EP | 0 622 046 A2 | 7/2001 |
| EP | 1 112 717 A1 | 7/2001 |

OTHER PUBLICATIONS

Ash et al., "A Subcutaneous Capillary Filtrate Collector for Measurement of Blood Chemistries", ASAIO Journal, 1993.
Brace et al., "Re-evaluation of the Needle Method for Measuring Interstitial Fluid Pressure", American Journal of Physiology, 1975.
Ginsberg, "An Overview of Minimally Invasive Technologie", Clinical Chemistry, 1992.
Janle-Swain et al., "Use of a Capillary Filtrate Collector for Monitoring Glucose in Diabetics", ASAIO Journal, 1987.
Kayashima et al., "Suction Effusion Fluid from Skin and Constituent Analysis: New Candidate for Interstitial Fluid", American Journal of Physiology, 1992.
Turner et al., "Diabetes Mellitus: Biosensors for Research and Management", Biosensors, 1985.
JP 09-084781 Machine Translation.
U.S. Appl. No. 10/607,347 Office Action mailed Apr. 29, 2009.
U.S. Appl. No. 10/607,347 Office Action mailed Sep. 2, 2009.
U.S. Appl. No. 11/353,849 Office Action mailed Feb. 2, 2009.
Ash et al., "A Subcutaneous Capillary Filtrate Collector for Measurement of Blood Glucose", ASAIO Journal, 1992, vol./Issue No. 38 (3), pp. M416-M420, J.B. Lippincott Co.
Brace et al., "Re-evaluation of the Needle Method for Measuring Interstitial Fluid Pressure", American Journal of Physiology, 1975, vol./Issue No. 229 (3), pp. 603-607, American Physiological Society.
DE 35 08 365 A1 English Abstract.
Final Office Action mailed Mar. 11, 2009 in related U.S. Appl. No. 10/835,094.
FR 2 590 673 English Abstract.
GB 8818491A Patent Application.
Ginsberg, "An Overview of Minimally Invasive Technologies", Clinical Chemistry, 1992, vol./Issue No. 38 (9), pp. 1596-1600, Becton Dickinson and Co.

Janle-Swain et al., "Use of a Capillary Filtrate Collector for Monitoring Glucose in Diabetics", ASAIO Journal, 1987, pp. 336-340, J.B. Lippincott Co.

JP 2000-152923 A English Abstract.

JP 2001-095787 A English Abstract.

JP H02-120655 English Language Abstract.

JP H02-170388 A English Abstract.

JP H06-004150 A English Abstract.

JP H09-089885 A Translation.

JP H09-294737 A Machine Translation.

Kayashima et al., "Suction Effusion Fluid from Skin and Constituent Analysis: New Candidate for Interstitial Fluid", American Journal of Physiology, 1992, vol./Issue No. 263 (5), pp. H1623-H1627, American Physiological Society.

Korthuis, R.J. et al., "Interstitium & Lymphatic Techniques", Microcirculatory Technology, 1986, pp. 317-340, Academic Press, Inc.

Office Action from United States Patent Office dated Oct. 5, 2007, U.S. Appl. No. 10/165,102, filed Jun. 7, 2002, First Named Inventor: Perez, Devices and Methods for the Expression of Bodily Fluids From an Incision.

Office Action received in counterpart U.S. Appl. No. 10/753,973 mailed Dec. 26, 2008.

Turner et al., "Diabetes Mellitus: Biosensors for Research and Management", Biosensors, 1985, vol./Issue No. 1 (1), pp. 85-115, Elsevier Applied Science Publishers, UK.

U.S. Appl. No. 10/753,973 Office Action mailed Jul. 28, 2009.

Wiig, Helge, "Evaluation of Methodologies for Measurement of Interstitial Fluid Pressure (Pi): Physiological Implications of Recent Pi Data", Critical Reviews in Biomedical Engineering, 1990, vol./Issue No. 18-1, pp. 27-54, CRC Press, Boca Raton, Florida.

WO 1991/06855 A2 Machine Translation.

* cited by examiner

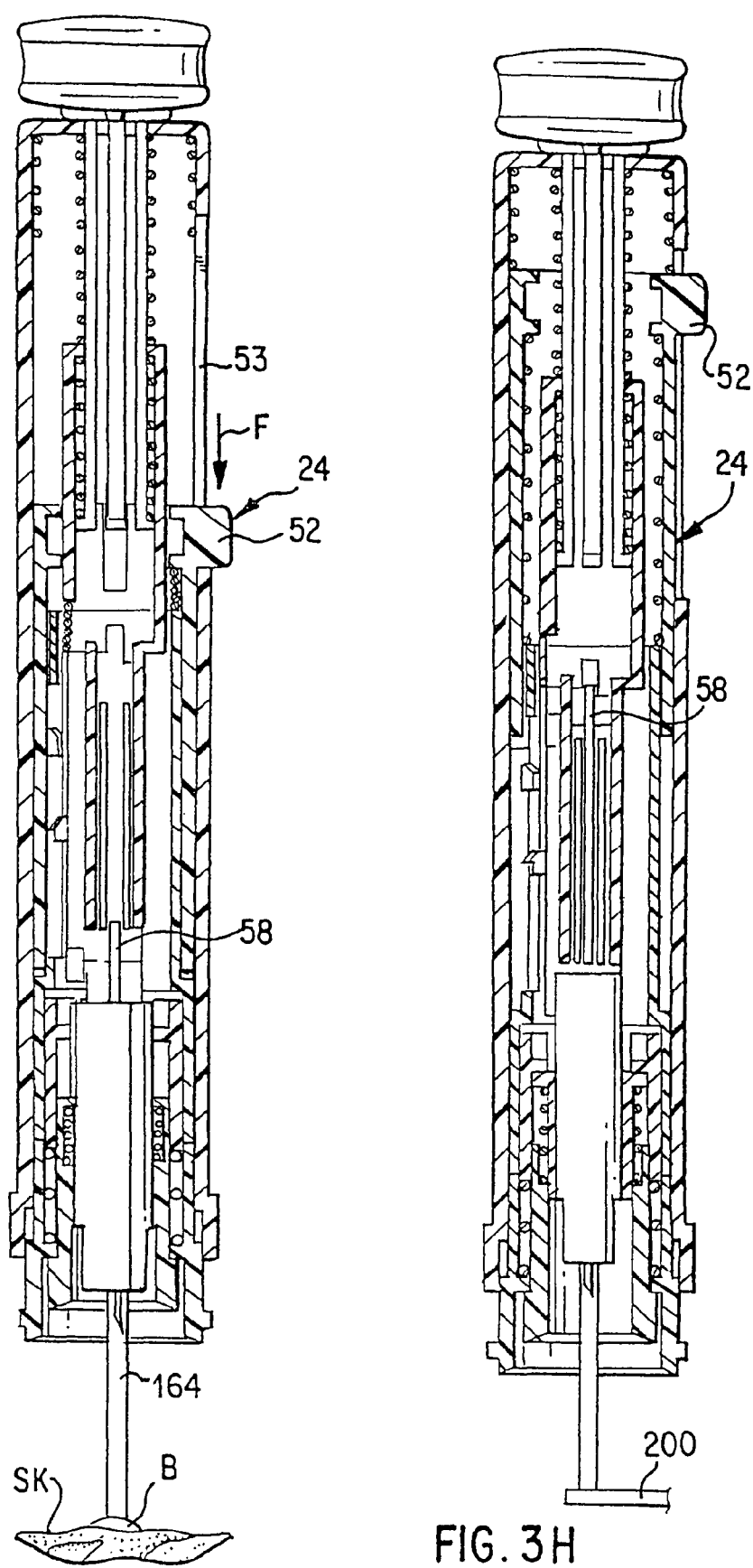

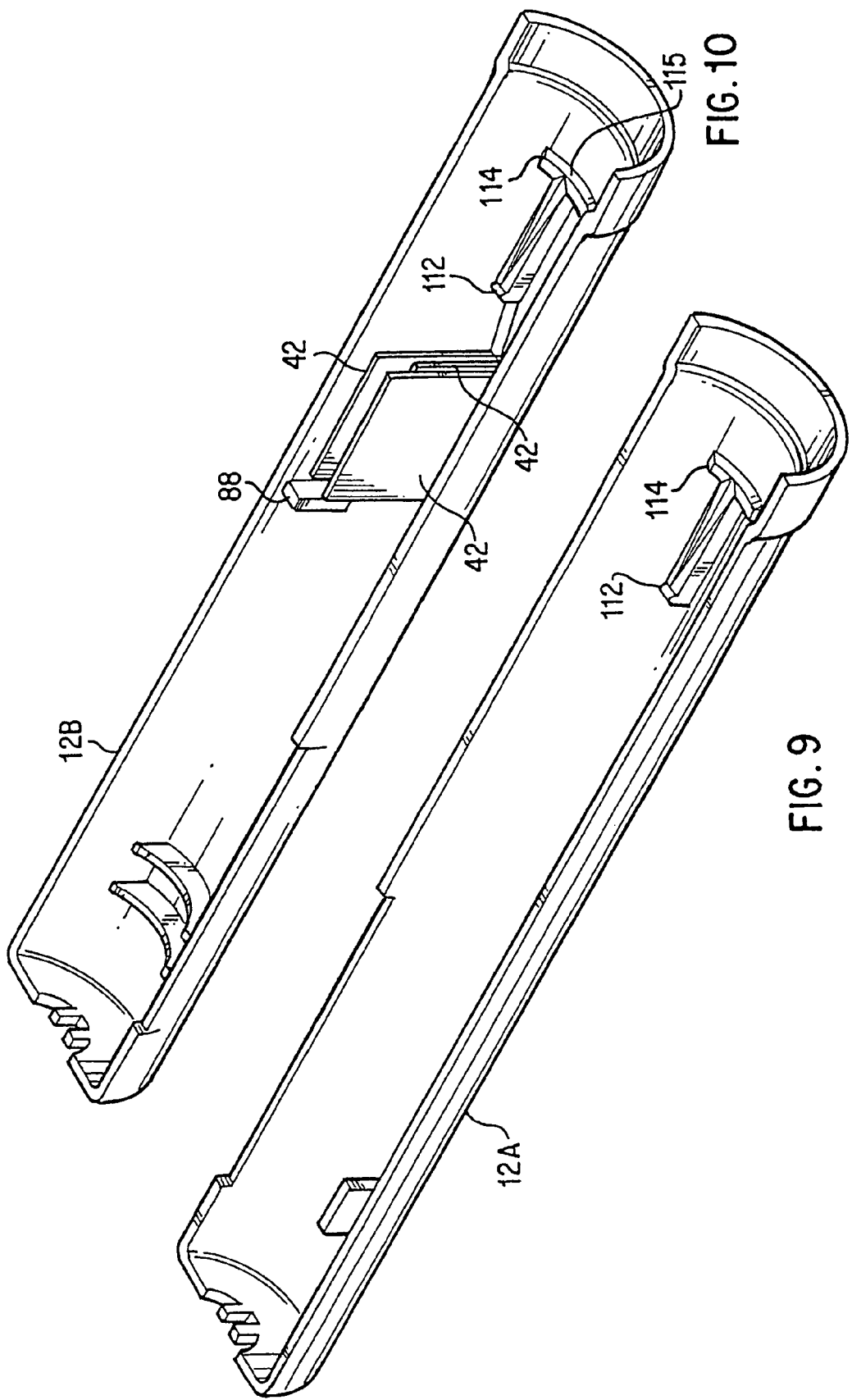

BODY FLUID SAMPLING DEVICE AND METHODS OF USE

PRIOR APPLICATIONS

This application is a continuation of application Ser. No. 10/128,780 filed Apr. 23, 2002, which is a continuation of application Ser. No. 09/528,097 filed Mar. 17, 2000, which is a continuation of application Ser. No. 09/204,909 filed Dec. 3, 1998 now U.S. Pat. No. 6,056,701, which is a continuation of application Ser. No. 08/857,680 filed May 16, 1997 now U.S. Pat. No. 5,879,311, which claims benefit of applications Serial No. 60/017,133 filed May 17, 1996; No. 60/019,918 filed Jun. 14, 1996; No. 60/023,658 filed Aug. 1, 1996; No. 60/025,340 filed Sep. 3, 1996; No. 60/092,121 filed Sep. 16, 1996; No. 60/064,856 filed Sep. 17, 1996; and No. 60/044,406 filed Oct. 8, 1996; the disclosures of which are incorporated herein by reference. The present invention is related to inventions disclosed in the following concurrently filed, commonly assigned U.S. applications: Ser. No. 08/858,045, entitled "Methods and Apparatus For Sampling Body Fluid"; Ser. No. 08/857,335, entitled "Disposable Element for Use in a Body Fluid Sampling Device"; Ser. No. 08/858,043 entitled "Methods and Apparatus for Sampling and Analyzing Body Fluid"; and Ser. No. 08/858,043, entitled "Methods and Apparatus for Expressing Body Fluid from an Incision". The disclosures of those applications are incorporated herein by reference.

FIELD OF THE INVENTION

The present invention relates to lancing devices and methods for obtaining samples of blood and other fluids from the body for analysis or processing.

BACKGROUND OF THE INVENTION

Many medical procedures in use today require a relatively small sample of blood, in the range of 5-50 µL. It is more cost effective and less traumatic to the patient to obtain such a sample by lancing or piercing the skin at a selected location, such as the finger, to enable the collection of 1 or 2 drops of blood, than by using a phlebotomist to draw a tube of venous blood. With the advent of home use tests such as self monitoring of blood glucose, there is a requirement for a simple procedure which can be performed in any setting by a person needing to test.

Lancets in conventional use generally have a rigid body and a sterile needle which protrudes form one end. The lancet may be used to pierce the skin, thereby enabling the collection of a blood sample from the opening created. The blood is transferred to a test device or collection device. Blood is most commonly taken from the fingertips, where the supply is generally excellent. However, the nerve density in this region causes significant pain in many patients. Sampling of alternate sites, such as earlobes and limbs, is sometimes practiced to access sites which are less sensitive. These sites are also less likely to provide excellent blood samples and make blood transfer directly to test devices difficult Repeated lancing in limited surface areas (such as fingertips) results in callous formation. This leads to increased difficulty in drawing blood and increased pain.

To reduce the anxiety of piercing the skin and the associated pain, many spring loaded devices have been developed. The following two patents are representative of the devices which were developed in the 1980's for use with home diagnostic test products.

Cornell et al. U.S. Pat. No. 4,503,856 describes a spring loaded lancet injector. The reusable device interfaces with a disposable lancet. The lancet holder may be latched in a retracted position. When the user contacts a release, a spring causes the lancet to pierce the skin at high speed and then retract. The speed is important to reduce the pain associated with the puncture.

Levin et al. U.S. Pat. No. 4,517,978 describes a blood sampling instrument. This device, which is also spring loaded, uses a standard disposable lancet. The design enables easy and accurate positioning against a fingertip so the impact site can be readily determined. After the lancet pierces the skin, a bounce back spring retracts the lancet to a safe position within the device.

In institutional settings, it is often desirable to collect the sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

Haynes U.S. Pat. No. 4,920,977 describes a blood collection assembly with lancet and microcollection tube. This device incorporates a lancet and collection container in a single device. The lancing and collection are two separate activities, but the device is a convenient single disposable unit for situations when sample collection prior to use is desirable. Similar devices are disclosed in Sarrine U.S. Pat. No. 4,360,016, and O'Brien U.S. Pat. No. 4,924,879.

Jordan et al. U.S. Pat. No. 4,850,973 and No. 4,858,607, disclose a combination device which may be alternatively used as a syringe-type injection device and a lancing device with disposable solid needle lancet, depending on configuration.

Lange et al. U.S. Pat. No. 5,318,584 describes a blood lancet device for withdrawing blood for diagnostic purposes. This invention uses a rotary/sliding transmission system to reduce the pain of lancing. The puncture depth is easily and precisely adjustable by the user.

Suzuki et al. U.S. Pat. No. 5,368,047, Dombrowski U.S. Pat. No. 4,653,513 and Ishibashi et al. U.S. Pat. No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device.

Garcia et al. U.S. Pat. No. 4,637,403 and Haber et al. U.S. Pat. No. 5,217,480, disclose combination lancing and blood collection devices which use a diaphragm to create a vacuum over the wound site.

Erickson et al. U.S. Pat. No. 5,582,184 describes a means of collecting and measuring body fluids. This system uses a coaxial syringe and capillary tube disposed within a spacer member. The spacer member limits the depth of syringe penetration, and compresses body tissue around the syringe while the syringe is in the skin, for improving the flow of interstitial fluid to the incision. However, it will be appreciated that the incision will tend to close against the syringe, thereby limiting any advantage that can be achieved.

Single use devices have also been developed for single use tests, i.e. home cholesterol testing, and for institutional use to eliminate cross-patient contamination multi-patient use. Crossman et al. U.S. Pat. No. 4,869,249, and Swierczek U.S. Pat. No. 5,402,798, also discloses disposable, single use lancing devices.

U.S. Pat. Nos. 5,421,816; 5,445,611; and 5,458,140 disclose, as a replacement for invasive sampling, the use of ultrasound to act as a pump for expressing interstitial fluid directly through intact (non-lanced) skin. The amount of fluid which can be obtained in that way is very limited, however.

The disclosures of the above patents are incorporated herein by reference.

Even with the many improvements which have been made, the pain associated with lancing remains a significant issue for many patients. The need for blood sampling and the fear of the associated pain is also a major obstacle for the millions of diagnosed diabetics, who do not adequately monitor their blood glucose due to the pain involved. Moreover, lancing to obtain a blood sample for other diagnostic applications is becoming more commonplace, and a less painful, minimally invasive device is needed to enhance those applications and make those technologies more acceptable.

An object of the present invention therefore, is to provide a device and a method for obtaining a sample of bodily fluid through the skin which is virtually pain free and minimally invasive.

Furthermore, known lancing devices include manually actuable buttons for triggering the lance-driving mechanism once the user has placed the device against his/her skin. Because the user knows the precise instant when the lancet will be triggered, there is a tendency for the user to jerk or raise the device at the instant of triggering, which can lead to inconsistent skin penetration, or possibly no penetration. Therefore, a further object of the invention is to provide a lancing device which eliminates such a tendency on the part of the user.

Moreover, known carriers for supporting disposable lancets are configured to permit the disposable lancet member to be inserted and removed solely through a lower end thereof. That requires that a user grasp a lower portion of the disposable lancet member in order to push it upwardly or pull it downwardly. Since the needle projects from a lower end of the disposable lancet member, the user's hand will be in the immediate vicinity of the needle, and thus exposed to potential injury and/or contamination. Also, the disposable lancet member is typically held in the carrier by friction fit. Due to normal manufacturing tolerances, it is difficult to ensure a sufficiently tight fit for the disposable lancet member; there may be a tendency for the disposable lancet member to wobble, thereby increasing the amount of pain inflicted during a lancing step.

Therefore, it is another object of the invention to provide a lancet carrier which eliminates the above-mentioned shortcomings.

An additional object of the invention is to make a lancing device safer by preventing the lancet-driving mechanism from being cocked until the disposable has been inserted therein.

Another object of this invention is to provide a method which can result in a sample of either blood or intersticial fluid, depending on the sample site and the penetration depth utilized. While there are no commercially available devices utilizing interstitial fluid (ISF) at this time, there are active efforts to establish the correlation of analytes, such as glucose, in ISF compared to whole blood. If ISF could be readily obtained and correlation is established, ISF may be preferable as a sample since there is no interference of red blood cells or hematocrit adjustment required.

Another object of this invention is to provide a method which can draw a small but adjustable sample, i.e. 3 µL for one test device and 8 µL for another test device, as appropriate.

Another object of this invention is to provide a method by which the drawn sample is collected and may be easily presented to a testing device, regardless of the location of the sample site on the body. This approach helps with infection control in that multiple patients are not brought in contact with a single test instrument; only the sampling device with a disposable patient-contact portion is brought to the test instrument. Alternatively, the disposable portion of a test device may be physically coupled with the sampler so the sample can be brought directly into the test device during sampling. The test device may then be read in a test instrument if appropriate or the testing system can be integrated into the sampler and the test device can provide direct results displayed for the patient.

It is a further object of the invention is to provide a device for minimally invasive sampling comprising a reusable sampler and disposable lancet member and sample collection device.

SUMMARY OF THE INVENTION

One aspect of the present invention involves a lancing device for lancing skin to sample blood or interstitial fluid. The device comprising a housing. A lancet carrier is mounted adjacent a front end of the housing for longitudinal movement relative thereto. A cockable spring-biased hammer mechanism is provided for pushing the lancet carrier forwardly to lance the skin. A latch is provided for releasably retaining the hammer mechanism in a cocked position. A latch-releasing mechanism includes a skin-contacting portion for being rearwardly displaced in response to being pressed against the skin, and a latch-releasing portion for releasing the latch in response to the rearward displacement of the skin contacting portion.

In another aspect of the invention, a safety mechanism is provided which is normally disposed in a safety position for preventing the hammer mechanism from being cocked, and being movable to a non-safety position in response to installation of the lancet carrier into the housing for enabling the hammer mechanism to be cocked.

In another aspect of the invention, a disposable lancet comprises a body which houses a skin lancing member and a capillary tube. A pusher member is provided for pushing the capillary tube forwardly relative to the body after the skin has been lanced, for drawing-in fluid from the lanced skin.

Yet another aspect of the invention relates to the combination of a disposable lancet and a carrier therefor. The carrier comprises a sleeve adapted to be mounted in a housing. The sleeve includes an internal surface forming a through passage extending from an upper end to a lower end of the sleeve. The disposable lancet is seated in the through passage. The internal surface is configured to permit insertion and removal of the disposable lancet solely through the upper end. The internal surface includes at least one upwardly facing shoulder on which the disposable lancet is supported. The invention also relates to the lancet carrier per se.

Another aspect of the invention relates to a sampling device for sampling body fluid. The sampling device comprises a housing defining a longitudinal axis, and an incision-forming means for forming an incision through the skin surface. A stimulator member is mounted at a forward end of the housing and is depressible against the skin to depress a ring of body tissue in surrounding relationship to the skin for urging body fluid toward and outwardly through the incision, to form a drop of body fluid at an open end of the incision. A pusher member is provided for moving the capillary tube forwardly relative to the carrier for drawing-in the body fluid.

A method aspect of the invention involves the steps of abutting a forward end of a housing against a skin surface of a user's body, and forming an incision through the skin surface. The housing is pressed against the skin surface to repeatedly depress a ring of body tissue in surrounding relationship to the incision to urge body fluid toward and outwardly through the incision to form a drop of body fluid at an open end of the incision. The capillary tube is extended forwardly relative to the carrier, and a forward end of the capillary tube is inserted into the drop of body fluid.

BRIEF DESCRIPTION OF THE DRAWINGS

The objects and advantages of the invention will become apparent from the following detailed description of a preferred embodiment thereof in connection with the accompanying drawing in which like numerals designate like elements and in which:

FIGS. 3A-3H are longitudinal sectional views taken through the lancing device and depicting the device in various stages of operation;

FIG. 9 is a perspective view of one-half of a housing part according to the present invention;

FIG. 10 is a perspective view of the other housing part according to the invention;

DETAILED DESCRIPTION OF A PREFERRED EMBODIMENT OF THE INVENTION

Figure 1:
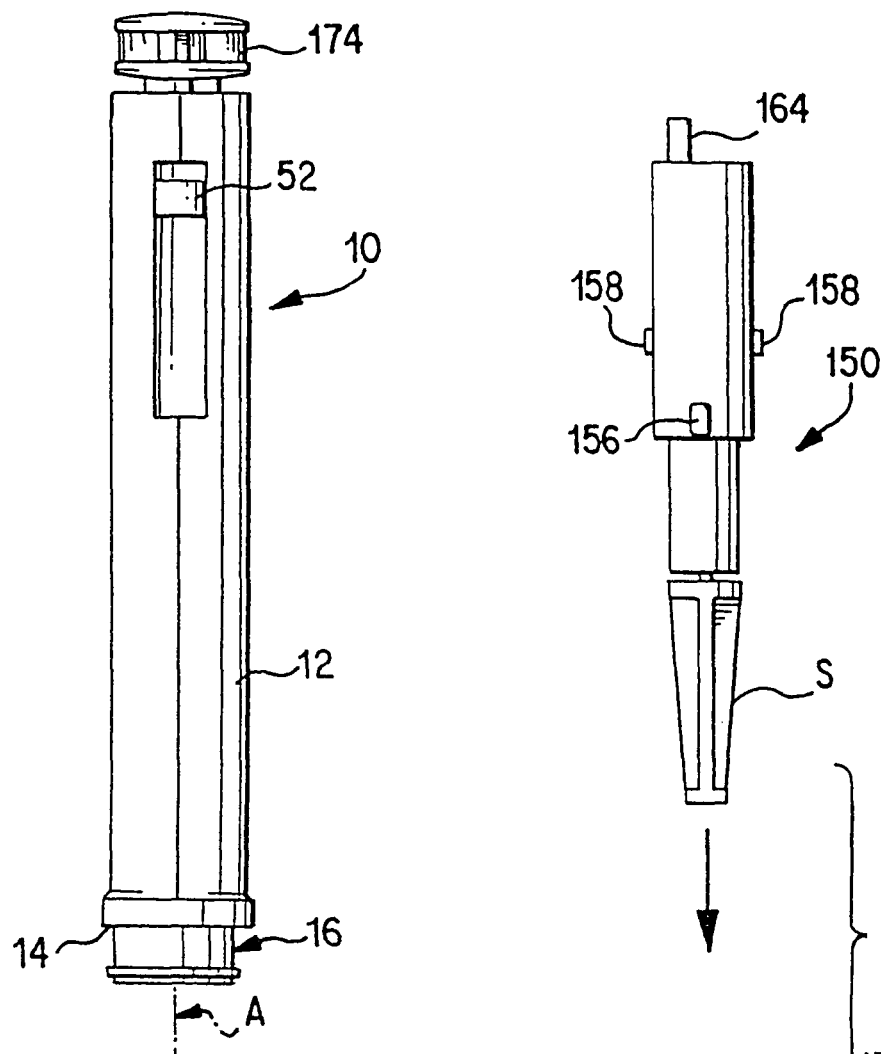
FIG. 1 is a side elevational view of a lancing device according to the present invention.

A minimally invasive sampling device 10 shown in FIG. 1, includes a tubular housing 12 formed of two half-shells 12A, 12B (see FIGS. 9 and 10) that are secured together. The housing 12 defines a longitudinal axis A and a lower open end 14 adapted to receive a removable lancet carrier unit 16. That carrier unit serves to carry a disposable lancet member 150 and to stimulate a skin puncture site, as will be explained subsequently.

Also mounted in the housing 12 (see FIG. 3A) are a hammer 18 for displacing the disposable lancet member downwardly in a skin-piercing direction, a manual handle 20 for raising the hammer to a cocked (i.e., downwardly biased) position, an interposer 22 for automatically releasing the hammer in response to a manual pushing of the device against a skin surface, a manually actuable pusher 24 for pushing a blood-receiving capillary tube downwardly, and a plurality of springs for achieving proper placement and movement of the above-described parts.

Figure 12:
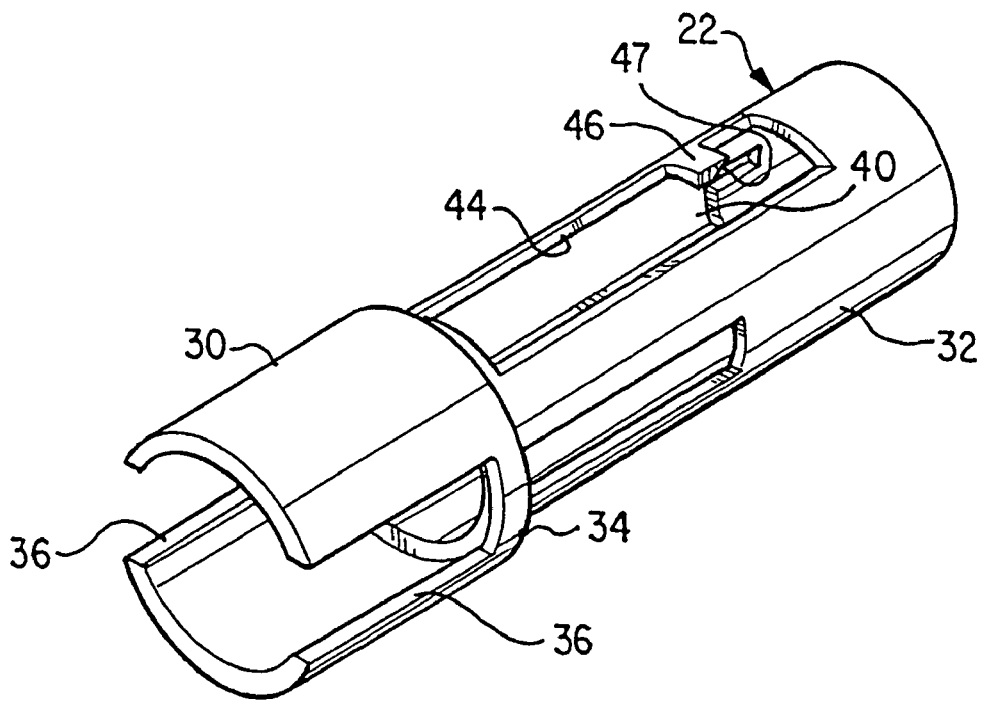
FIG. 12 is a bottom perspective view of an interposer member according to the present invention.
Figure 13:
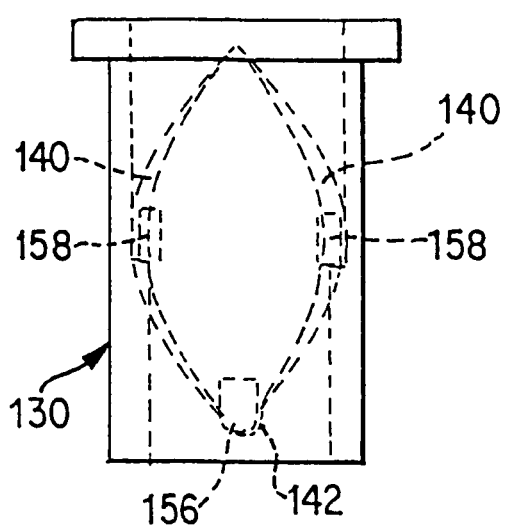
FIG. 13 is a side elevational view of a disposable carrier member according to the present invention, with projections of a disposable shown in phantom lines when the disposable is in an installed condition.
Figure 14:
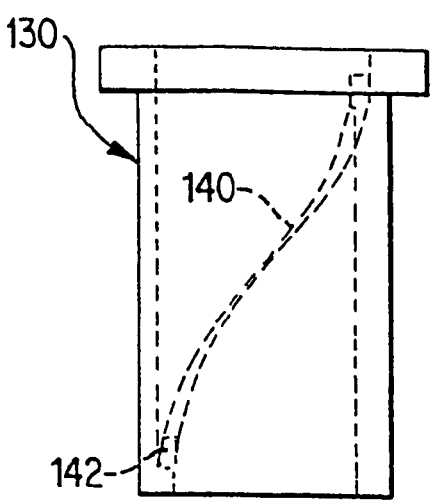
FIG. 14 is a side elevational view, taken from another angle, of the disposable carrier shown in FIG. 13.
Figure 15:
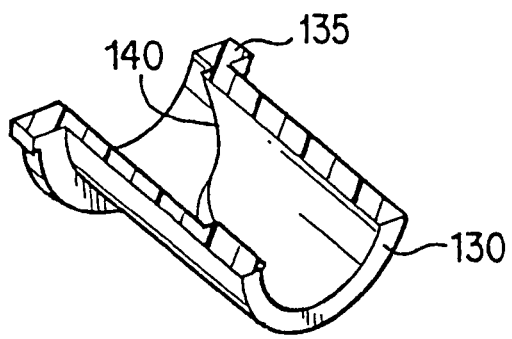
FIG. 15 is a sectional view taken through the carrier member of FIG. 13.
Figure 16:
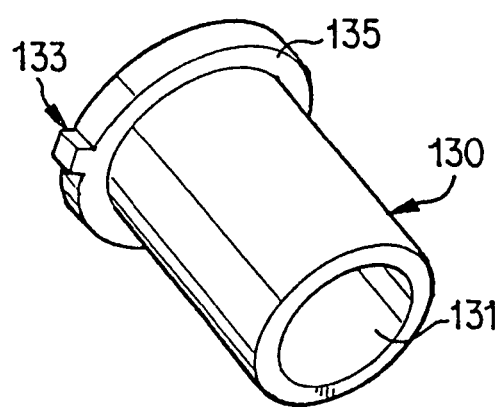
FIG. 16 is a bottom perspective view of the carrier of FIG. 13.

The interposer 22, shown in FIGS. 3 and 12, is longitudinally movable in the housing 12 and includes lower and upper cylindrical portions 30, 32, the lower portion being of smaller diameter than the upper portion to form an upwardly facing shoulder 34. A pair of diametrically opposed slits 36 is formed in the lower portion 30 for enabling the carrier unit 16 to be slid upwardly into the housing 12.

Formed in the upper portion 32 is a slot 40 through which project three longitudinally parallel guide ribs 42 (see FIG. 10) that are formed integrally with the inner surface of the housing shell 12B. A center one of the ribs 42 is shorter than the other two ribs 42 to form therewith a space into which an end of a capillary tube 164 can fit, as will be explained. Spaced ninety degrees from the slot 40 is another slot 44, and formed on a wall of that slot 44 is a triggering protrusion 46 having an inclined upper cam surface 47, which serves to release the hammer 18 from a cocked position as will be explained.

A coil compression spring 45 is disposed between an upper end of the interposer 22 and shoulders 47 formed on the pusher 24 to bias the interposer 22 downwardly.

Figure 4:
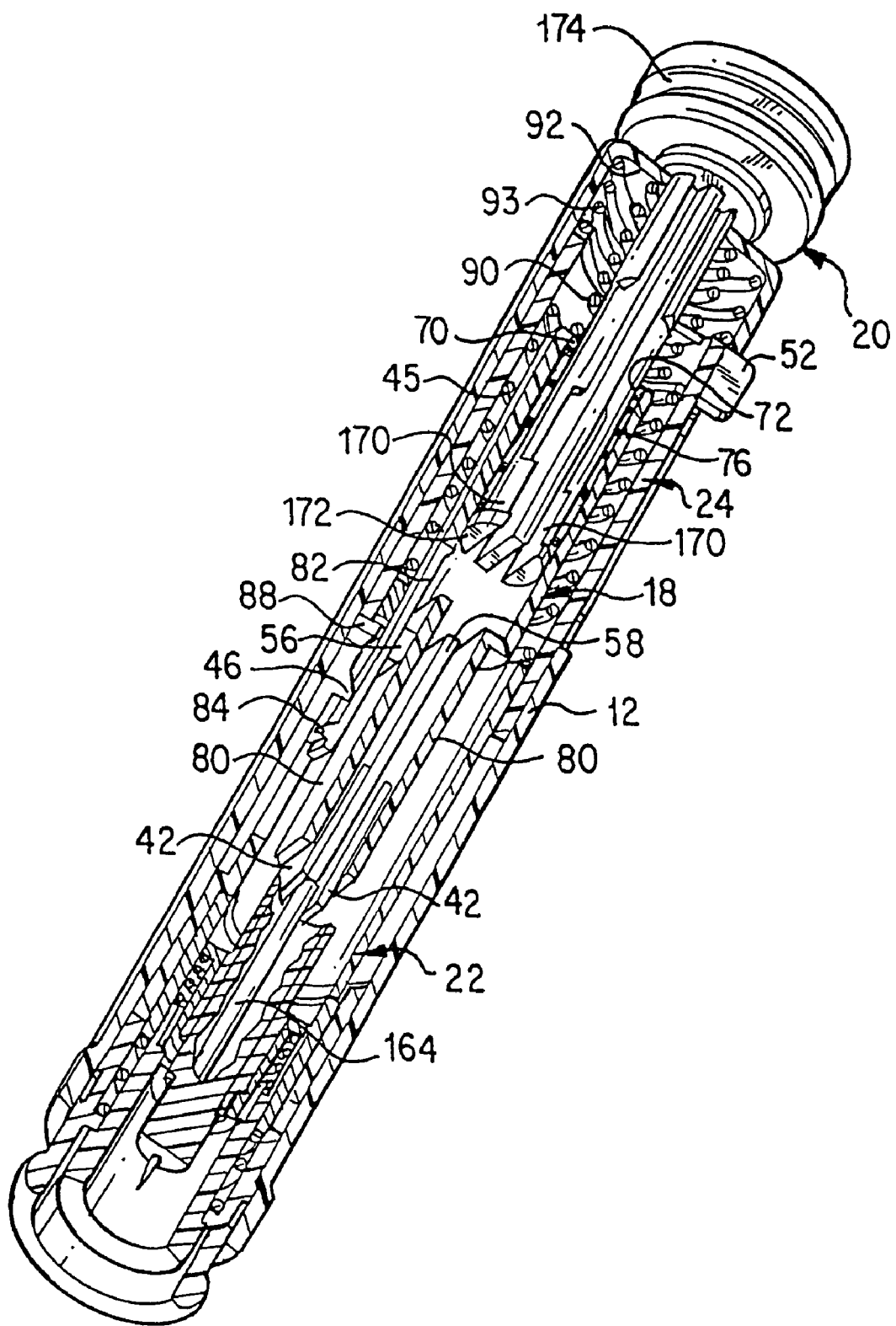
FIG. 4 is a longitudinal sectional perspective view of the lancing device according to the invention.
Figure 5:
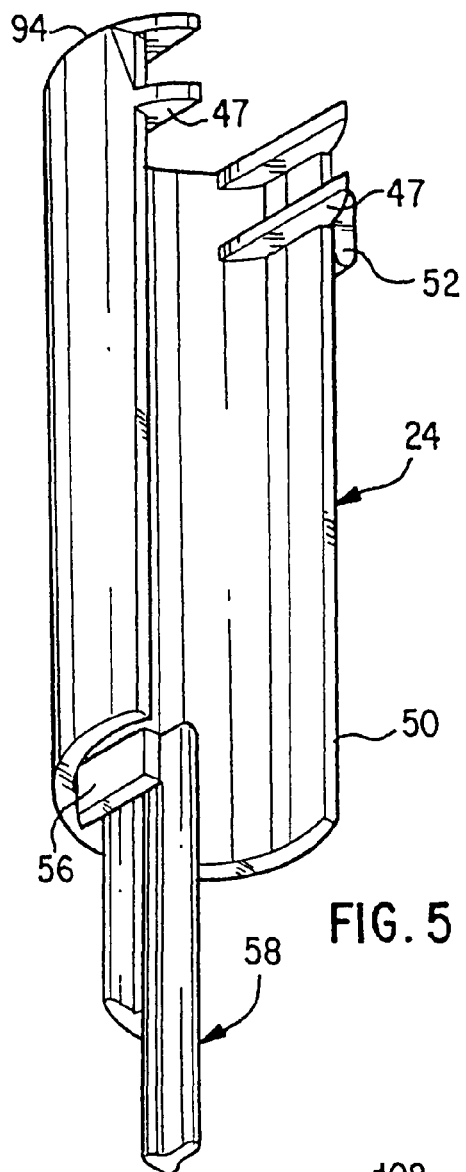
FIG. 5 is a bottom perspective view of a pusher member according to the invention.

The pusher 24, shown in FIG. 5, is longitudinally movable and includes a semi-cylindrical portion 50 having a knob 52 projecting radially outwardly from an upper end thereof. The knob 52 is sized to slide along a longitudinal slot 53 formed in the housing 12. Projecting radially inwardly from a lower end of an inner surface 54 of the portion 50 is a locking rib 56, and an actuating rib 58. The locking rib 56 and actuating rib 58 project radially inwardly through the slot 40 formed in the interposer 22. The actuating rib 58 extends downwardly between the guide ribs 42 of the body 12, see FIGS. 4 and 11.

Figure 7:
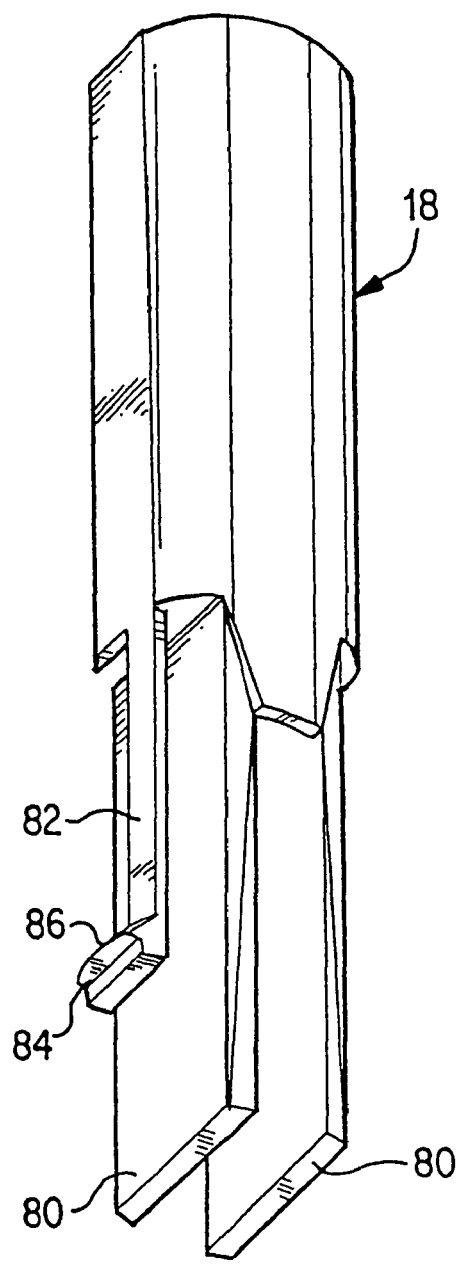
FIG. 7 is a bottom perspective view of a hammer member according to the present invention.
Figure 8:
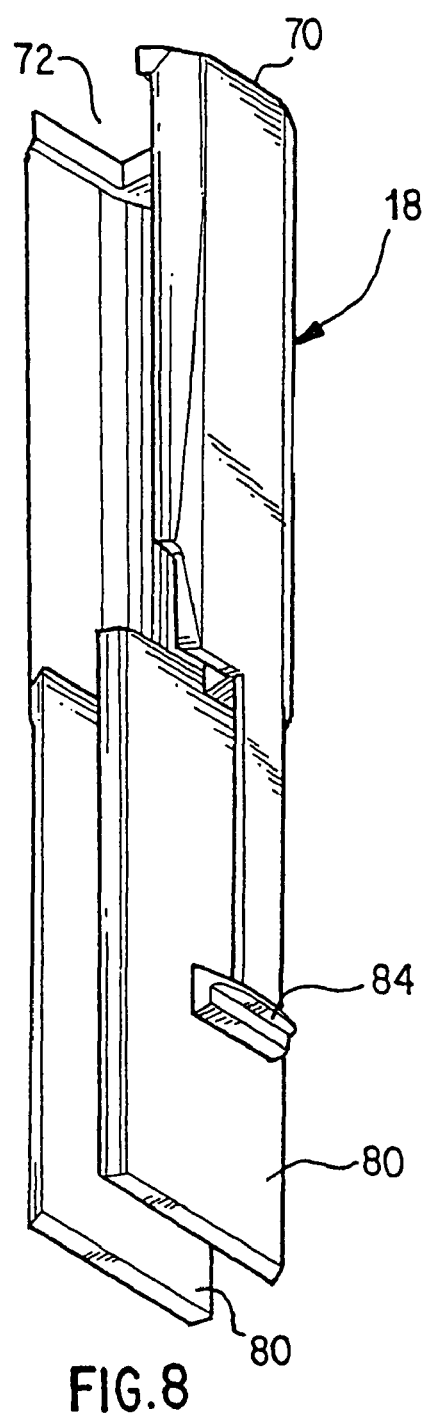
FIG. 8 is another bottom perspective view of the hammer member depicted in FIG. 7.

The hammer 18, shown in FIGS. 7 and 8, is longitudinally movable in the body 12, and includes a top wall 70 having an upper opening 72 to enable the handle 20 to be mounted therein. An upper portion 74 of the hammer 18 houses a coil compression spring 76 (see FIG. 3A) which serves as a recovery spring acting between the hammer and the handle 20, as will be explained. The lower portion of the hammer 18 comprises a latching arm 82, and a pair of parallel, longitudinal impact legs 80 which straddle the guide ribs 42 of the body 12. The latching arm 82 is spaced from one of the legs 80, to accommodate the locking rib 56 therebetween (see FIGS. 3A and 4). The latching arm 82 includes a radial outward finger 84 on its lower end, the top of which is defined by an inclined cam follower surface 86. As will be explained, the latching arm 82 is flexible in a radial direction when the finger 84 travels vertically past a stop 88 projection which projects radially inwardly from the inner surface of the housing 12 as the hammer is being raised to a cocked position (see FIG. 3E).

Figure 3A:
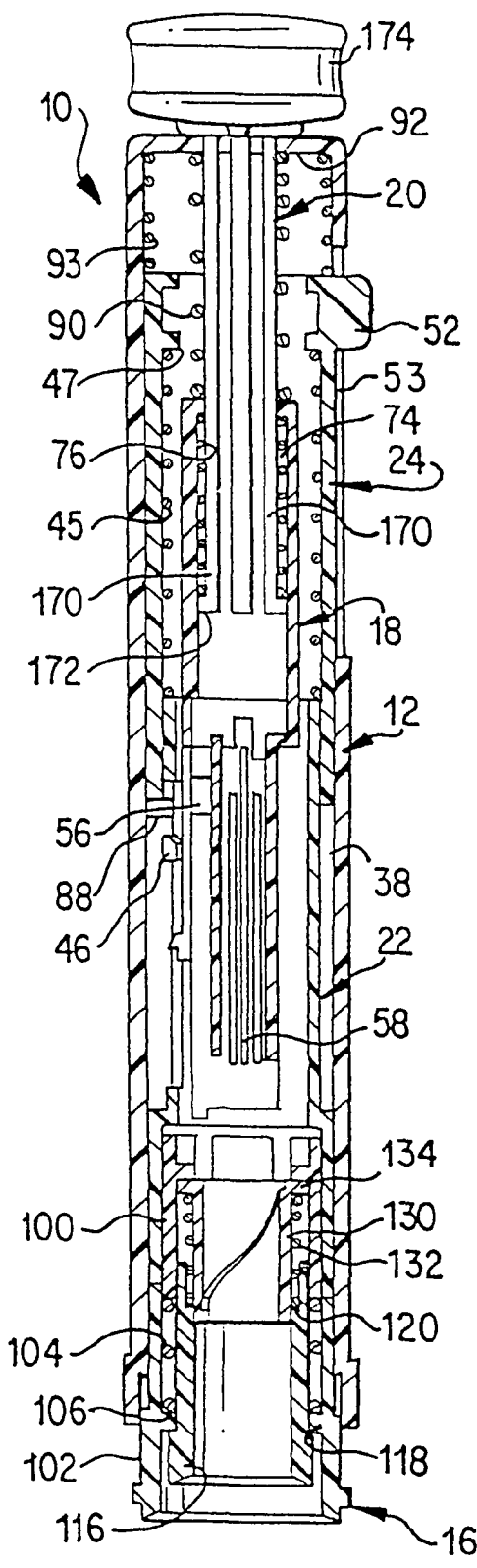

A coil compression spring 90 acts between an upper wall 92 of the body 12 and the top wall 70 of the hammer 18 to bias the hammer downwardly (see FIG. 3A). A coil compression spring 93 surrounding the spring 90 acts between the upper wall 92 and an upper edge 94 of the pusher 24 to bias the pusher downwardly.

Figure 2:
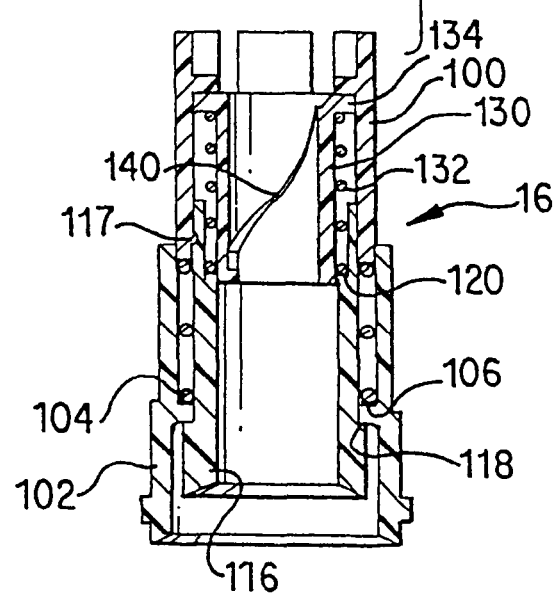
FIG. 2 is a side elevational view of a disposable being inserted into a lancet carrier unit, with the lancet carrier unit being shown in longitudinal section.
Figure 6:
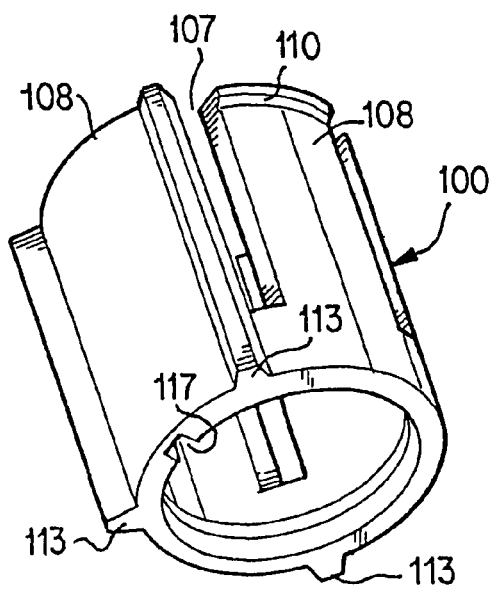
FIG. 6 is a bottom perspective view of an adapter member according to the present invention.

The carrier unit 16 includes an adapter 100 depicted in FIGS. 2 and 6. The adapter 100 is generally cylindrical and is telescopingly disposed within a stimulator sleeve 102. A coil compression spring 104 is interposed between a lower edge of the adapter 100 and an annular flange 106 projecting radially inwardly from an inner surface of the sleeve 102. The adapter 100 includes a plurality of longitudinal slots 107 dividing the adaptor into a plurality of spring fingers 108, two of which have a circumferential groove 110 formed in an upper portion thereof. The grooves are configured to receive projections 112 which are formed integrally on inner surfaces of the housing shells 12A, 12B, in order to releasably secure the adapter within the housing 12. That is, if a downward force is applied to the adapter, the spring fingers 108 will yield and permit the adapter to be removed from the housing 12.

The adapter 100 also includes three radially outwardly projecting keys 113 arranged to engage respective sides 114 of protrusions 115 formed on inner surfaces of the housing shells 12A, 12B. The keys 113 and sides 114 are oriented such that the adapter can only enter the housing 12 in one specific circumferential orientation. A longitudinal keyway 117 is formed in an inner surface of the adapter for reasons to be explained.

Telescopingly mounted within the sleeve 102 is an inner ring 116 having a radially outwardly projecting shoulder 118 near its lower end, and a radially inwardly projecting should 120 formed near its upper end. The shoulder 118 is arranged to abut a lower end of the flange 106. The ring 116 includes an annular recess which receives a radial projection of the adapter 100 to form a snap-in connection 117 therebetween (see FIG. 2).

Situated coaxially within the adapter 100 and ring 116 is a lancet carrier 130 which is also depicted in FIGS. 13-16. The lancet carrier 130 is generally in the form of a cylindrical sleeve which includes a vertical through-passage 131 to enable a disposable lancet member 150 to be inserted downwardly thereinto when the carrier unit 16 has been removed from the housing 12. A coil compression spring 132 acts between a radial outer flange 134 of the lancet carrier 130 and the radially inner shoulder 120 formed on the ring 116.

The lancet carrier includes a pair of downwardly inclined, upwardly facing guide ramps 140 formed on its inner surface for guiding the disposable lancet member. Lower ends of the guide ramps 140 intersect to form an upwardly open recess 142. The ramps and recess form an upwardly facing seat on which the disposable lancet member is supported. A radially outwardly projecting key 133 is formed on an upper annular flange 135 of the carrier 130. That key 133 enters the keyway 117 of the adapter 100 to orient the carrier 130 circumferentially relative to the adapter.

Figure 11:
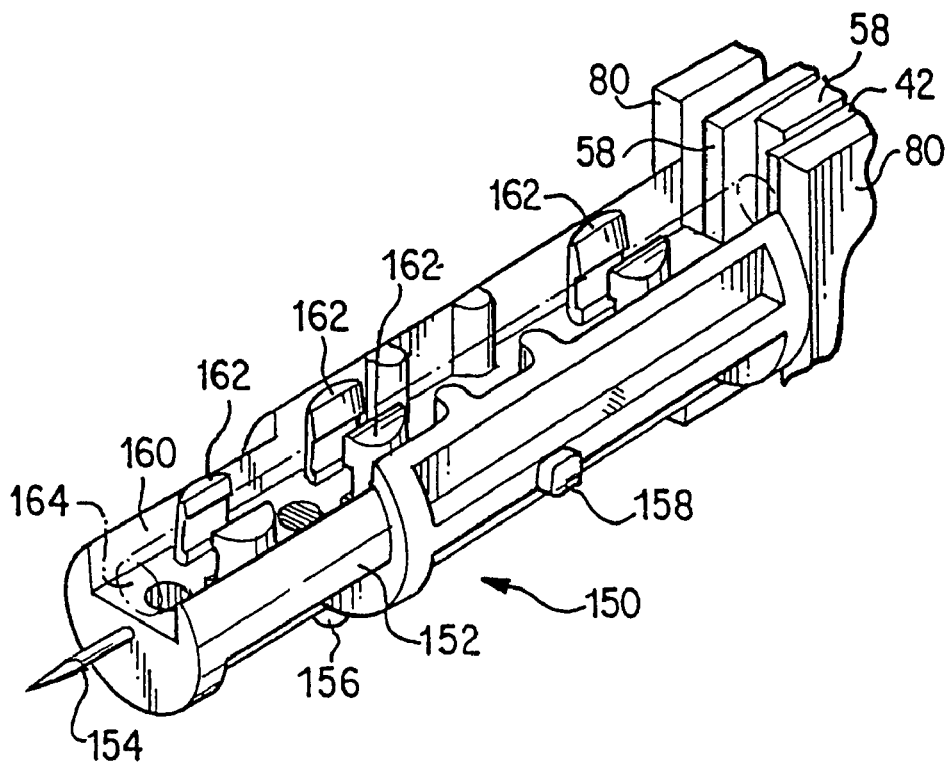
FIG. 11 is a perspective view of a disposable according to the invention, with a capillary tube shown in phantom.

The disposable lancet member 150 is depicted in FIGS. 2 and 11 and includes a generally cylindrical body 152 having a needle 154 projecting from its lower end. Projecting radially outwardly from an outer periphery of the disposable lancet member are three bosses 156 spaced circumferentially and longitudinally apart. That is, there are provided a lower boss 156, and a pair of upper bosses 158 disposed at the same elevation above the lower boss. The three bosses are spaced circumferentially apart from one another as the disposable lancet member is viewed in a longitudinal direction. When the disposable lancet member is dropped downwardly into an upper end of the lancet carrier 130 (see FIG. 2), the two upper projections engage respective ones of the two guide ramps 140 to guide downward motion of the disposable lancet member and ensure that the lower boss 156 enters the recess 142 (see also FIG. 13).

The disposable lancet member further includes a slot 160 extending longitudinally therealong. Disposed within the slot 160 are a plurality of pairs of opposed holding fingers 162 which are configured to frictionally grip the capillary tube 164 and retain the tube 164 in an orientation parallel to the longitudinal axis of the disposable lancet member, as shown in broken lines in FIG. 11. Due to the cooperation between the projections 156, 158 of the disposable lancet member and the guide ramps 140 of the lancet carrier 130, the capillary tube will be positioned in axial alignment with the actuating finger 58 of the pusher 24 when the unit 16 is inserted into the housing 12, for reasons to be explained.

The handle 20 (FIGS. 3A and 4) includes a pair of longitudinally extending lift fingers 170 which project downwardly through the top wall 70 of the hammer 18. Lower ends of the lift fingers constitute radially outwardly projecting feet 172 against which the lower end of the spring 76 bears. A manually grippable knob 174 is disposed at the top of the handle to enable a riser to raise the handle.

To explain the operation of the lancing device 10, attention is initially directed to FIG. 3A which depicts the device 10 in a condition where no disposable lancet member 150 is mounted in the carrier unit 16. To install a disposable lancet member, the carrier unit 16 is pulled downwardly from the housing, and a disposable lancet member 150 is dropped downwardly into the carrier 130 (see FIG. 2). In so doing, the bosses 156, 158 of the disposable lancet member ride along the guide ramps 140 of the lancet carrier until the lower boss 156 comes to rest in the recess 142 of the carrier. As a result, the capillary tube 164 of the disposable lancet member is oriented in a specific relationship with respect to the unit 16.

Figure 3B:
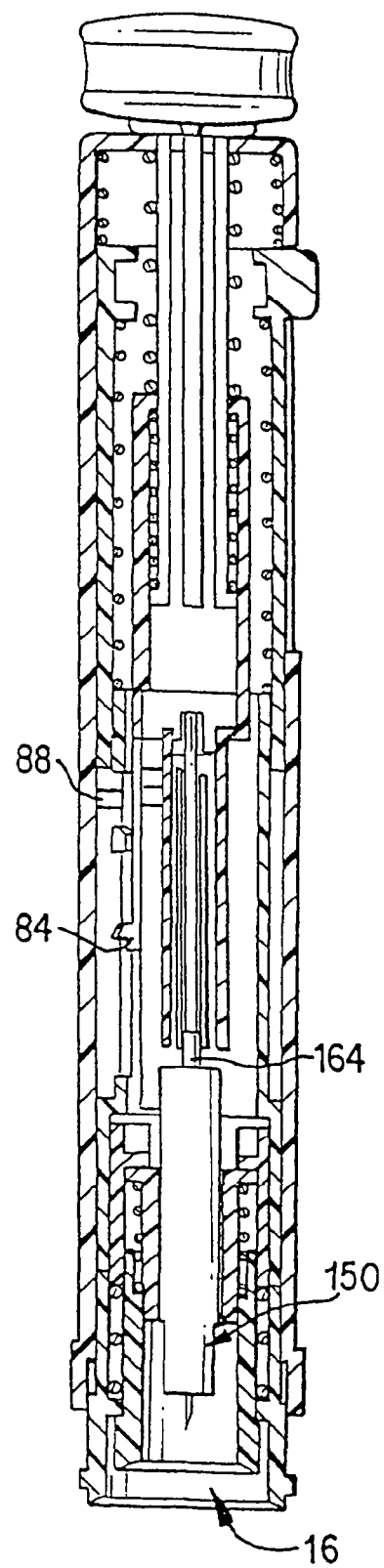

The unit 16 is then pushed longitudinally upwardly into the front end of the housing 12 until the grooves 110 formed in the spring fingers 108 of the adapter 100 snap onto the projections 112 of the housing 12, thereby locking the unit 16 in place (see FIG. 3B). Due to the relationship between the keys 113 on the adapter, and the sides 115 of the projections 114 formed on the housing 12, the adapter can be inserted in only one circumferential (rotary) relationship relative to the housing 12. Furthermore, since the circumferential relationship between the lancet holder 130 and the adapter 100 is pre-set by the engagement between the key 133 on the holder 130 and the keyway 117 on the adapter, it is ensured that the upper end of the capillary tube 164 is aligned with the actuating finger 58 of the pusher 24. Since the upper end of the capillary tube projects slightly upwardly past the upper end of the disposable lancet member 150 (see FIG. 3B), it pushes the actuating finger 58, and thus the entire pusher 24, slightly upwardly. In so doing, the locking rib 56 of the pusher is raised to a level above the stop 88 of the housing 12 for a reason which will become apparent.

Figure 3C:
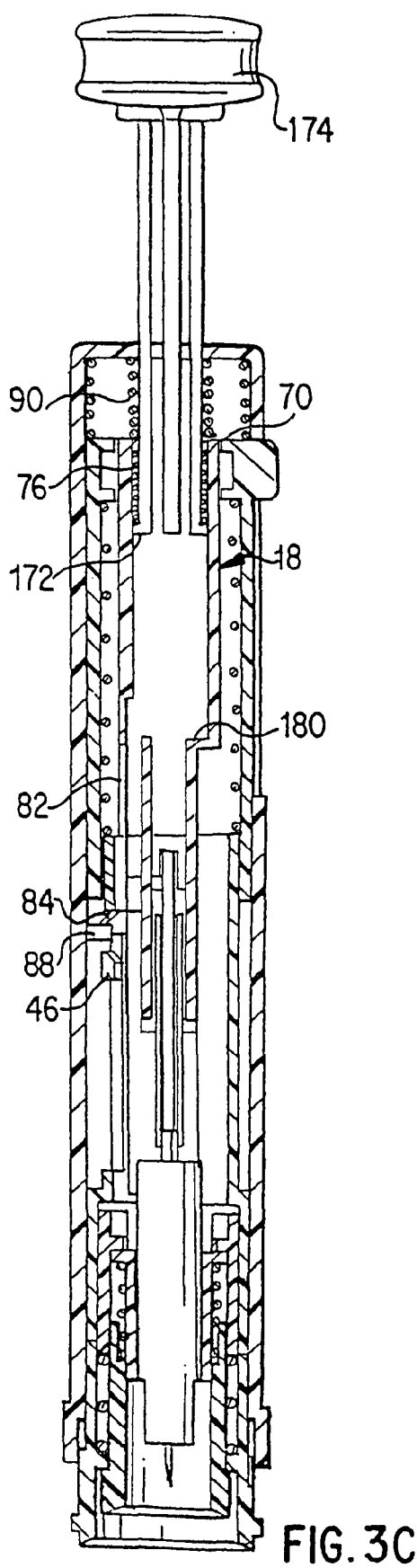
Figure 3D:
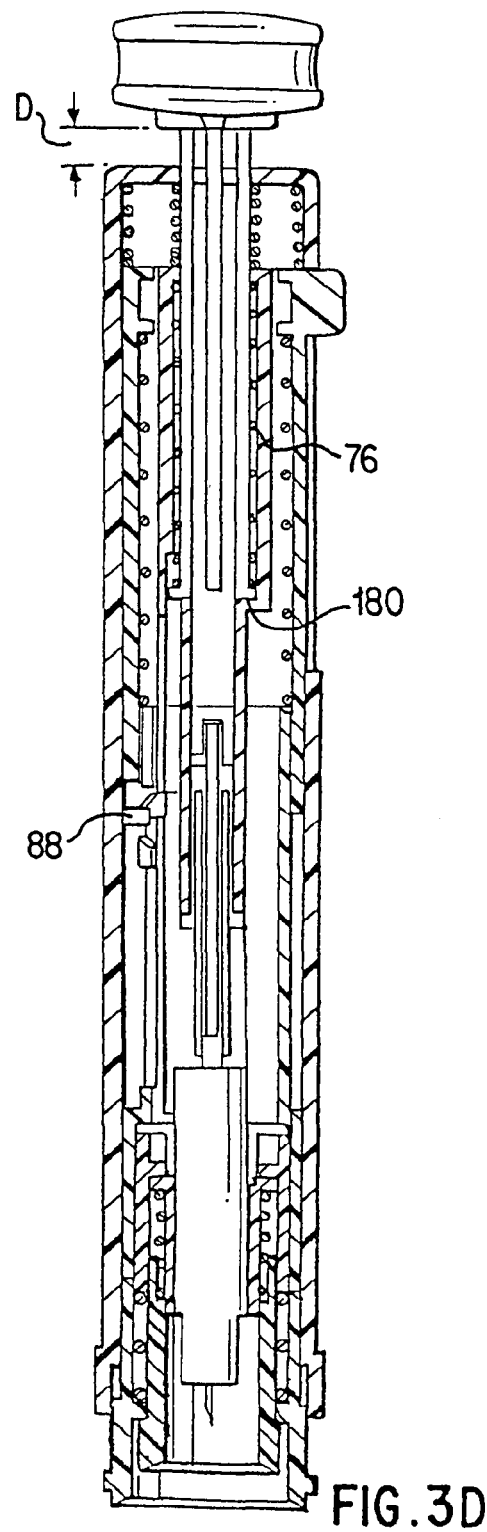
Figure 3E:
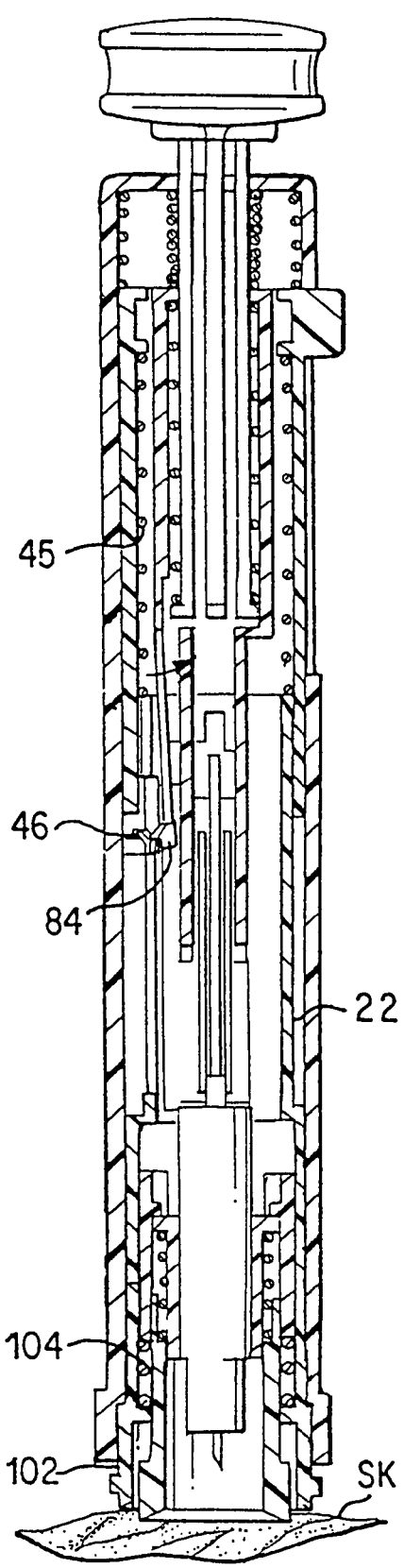
Figure 3F:
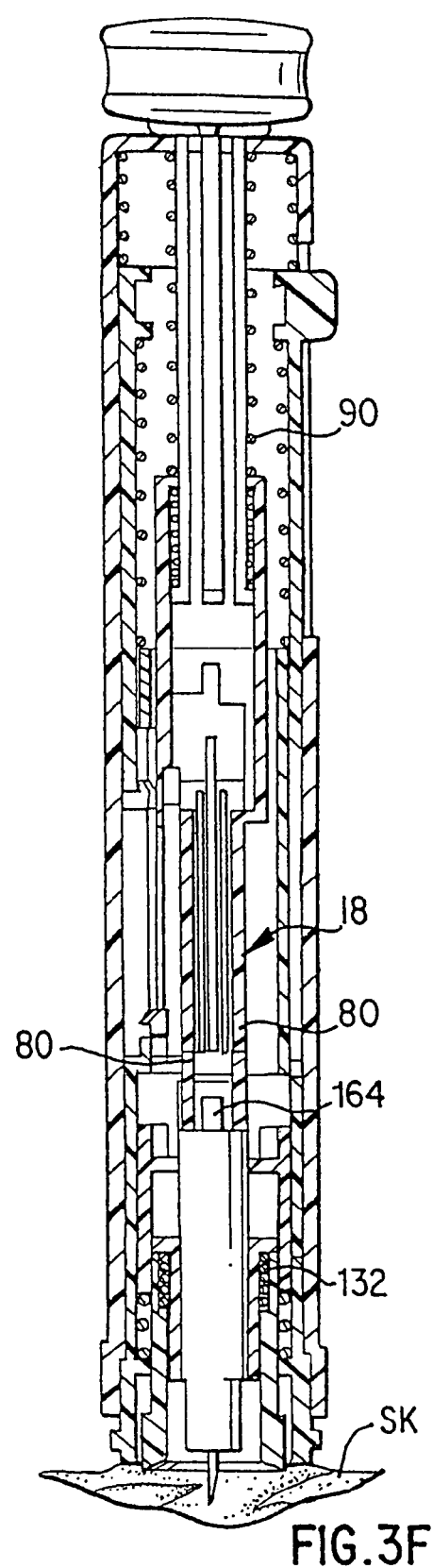

If a protective sheath S covers the needle 154 (see FIG. 2), it can be pulled off by the user who then grasps the knob 174 of the handle 20 and pulls upwardly thereon (FIG. 3C). This causes the spring 76 to be compressed between the feet 172 of the raising fingers 170 on the one hand, and the top wall 70 of the hammer 18. When the spring 76 bottoms out, further raising of the handle 20 causes the hammer 18 to be raised. Accordingly, the inclined surface 86 on the top of the latching finger 84 sequentially engages the undersides of the triggering protrusion 46 and the stop 88, causing the latching arm 82 to be flexed radially inwardly and allowing the finger 84 to pass over the protrusion 46 and then over the stop 88. Eventually, the finger 84 travels past the stop 88 and snaps radially outwardly, whereby downward movement of the finger (and thus of the hammer) is prevented by the top of the stop 88 (FIG. 3C).

It will be appreciated that had the locking rib 56 not been previously raised, the latching finger could not have been flexed radially inwardly. Therefore, the locking rib 56 ensures that the hammer 18 cannot be placed in an armed or cocked position unless a disposable lancet member 150 has been installed.

As the hammer 18 was raised, the spring 90 was simultaneously compressed, so now the hammer 18 is biased downwardly thereby.

When the handle 20 is released, the spring 76 pushes it downwardly (see FIG. 3D) until the feet 172 of the handle come to rest against a radially inwardly projecting shoulder 180 of the now-raised handle 18, whereby the knob 174 remains slightly raised by a distance D with respect to its previous position, serving as a visual indication that the hammer is cocked (armed).

When the stimulating sleeve 102 is pushed downwardly against the user's skin (FIG. 3E), the sleeve 102 becomes displaced upwardly against the bias of the spring 104, and raises the interposer 22 and its triggering protrusion 46 against the bias of spring 45. The triggering protrusion 46 is circumferentially offset with respect to the stop 88, so the protrusion is able to contact the underside of the latching finger 84 and cam it radially inwardly off the stop 88. This enables the previously-compressed spring 90 to displace the hammer 18 and its impact legs 80 downwardly opposite the bias of the spring 76 and against the disposable lancet member 150 (FIG. 3F), to push the disposable lancet member 150 and the carrier 130 downwardly opposite the bias of the spring 132, whereby the needle lances the skin. The carrier 130 and the disposable lancet member 150 are immediately withdrawn upwardly by the action of the spring 132. Such withdrawal is possible since the hammer 18 was immediately retracted by the spring 76. Thus, the lancing and retraction of the lancet is performed as a substantially continuous motion.

Next, the user repeatedly reciprocates the housing 12 up and down, whereby the stimulating sleeve 102 remains in contact with the skin but is repeatedly pressured by the spring 45 and repeatedly opens and closes the wound in a manner pumping fluid (such as blood) to the skin surface in the manner described in greater detail in application Ser. No. 08/858,043, the disclosure of which is incorporated by reference herein.

That is, each time that a downward force is applied, the end face of the outer stimulating sleeve exerts a downward force which depresses a ring-shaped portion of the skin and body tissue which is disposed in surrounding relationship to the wound or incision I, causing the wounded area to bulge while pulling apart the sides of the wound. Hence, fluid such as blood or interstitial fluid is trapped and pressurized so that it travels upwardly through the pulled-open end of the bulging wound since the surrounding ring of depressed skin and body tissue restricts the outward flow of fluid.

When the downward force is released, the sides of the wound close, and fresh fluid flows toward the area of the wound to replace fluid which had been forced upwardly through the wound. As the downward force is reapplied, the above-described action is repeated and additional fluid is forced through the wound. Eventually, this "pumping" action results in the formation of a suitably large drop B of body fluid.

Although the end face of the sleeve 102 is disclosed as being generally annular, it could be of other configurations such as oval or polygonal, whereby the ring of depressed body tissue would be similarly configured.

When a sufficiently large drop of fluid B has been developed at the skin surface (FIG. 3G), the user applies a downward force F to the knob 52 of the pusher 24 to displace the pusher and its actuating rib 58 downwardly against the bias of the spring 38. This pushes the capillary tube 164 downwardly until the lower end thereof projects from the bottom of the housing 12. At that point, the lower end of the capillary tube is placed in the drop of blood to draw blood thereinto by capillary action. The pusher 24 can be released, whereupon it will be displaced upwardly by the spring 38.

Then, a strip of material 200 can be brought into contact with the bottom of the capillary tube (FIG. 3H) to draw-out the fluid sample for analysis.

To perform a subsequent lancing/sampling operation, the user grasps the sleeve 102 and pulls out the carrier unit 16. The disposable lancet member 150 can then be lifted from the carrier 130 and discarded, whereupon a new disposable lancet member can be inserted.

Except for the needle 154 and the springs 93, 90, 45, 76, 104 and 132, the parts of the lancing device 10 are preferably formed of plastic.

It will be appreciated that the device 10 provides for an automatic triggering of the hammer in response to a pressing of the device against the skin. This eliminates any tendency for the user to jerk the device upwardly at the instant of triggering and ensures that penetrations of constant depth will be performed from one lancing operation to the next.

The ability of the device to prevent the hammer from being cocked unless a disposable lancet member has been installed provides assurance that the disposable lancet member will not be accidentally displaced forwardly as the carrier unit is being installed, as could otherwise occur if the hammer were in a cocked state during such installation. Hence, the user is protected against an accidental wounding.

The ability of the device to push-out the capillary tube for taking-in a fluid sample simplifies the sampling operation and minimizes the amount of direct manual handling of the capillary tube which is required. In fact, no direct contact with that tube need occur when using the device. This feature of the invention does not require the use of a lancet for making the incision. In lieu of using a lancet to make an incision, known pneumatic or hydraulic injectors of the type which inject pressurized gas or liquid against the skin could be used. Such auto injectors are sold by Becton-Dickinson, for example, to inject insulin. Be eliminating the insulin and merely injecting the gas (e.g., air or nitrogen) or liquid (e.g., water) at pressures above 30 psi, an incision could be formed in the skin for taking samples of body fluid. Advantageously, small particles could be mixed with the gas to promote the tissue-cutting action. The particles could comprise carbon particles of form 1 micron to 0.010 inches in diameter.

The ability to load and unload a disposable lancet member into the carrier unit through an upper end of that unit means that the user can keep his/her hands remote from the needle. This ensures against accidental wounding, possibly by a contaminated needle. The three-point securement of the disposable lancet member within the carrier as defined by the three projections of the disposable lancet member, creates a stable movement-free mounting of the disposable lancet member within the carrier unit. Hence, the disposable lancet member will not tend to move laterally during a lancing procedure, thereby reducing the amount of pain that may be experienced by the user.

Also, as explained in concurrently filed application Ser. No. 08/858,043, the ability of the device to pump body fluids such as blood or interstitial fluid to the skin surface enables the device to be used to lance the skin at areas of the body which are less susceptible to pain, such as the arm for example.

Although the present invention has been described in connection with a preferred embodiment thereof, it will be appreciated by those skilled in the art that additions, modifications, substitutions and deletions not specifically described may be made without departing from the spirit and scope of the invention as defined in the appended claims.

What is claimed is:

1. A method of sampling comprising:
   loading a disposable sampling module having a lancet and a capillary tube into a lancing device that includes a housing, wherein the capillary tube is located inside the housing during said loading the disposable;
   initiating a lancing cycle by pressing the housing of the lancing device against skin;
   lancing the skin to obtain a blood sample in response to said initiating the lancing cycle;
   collecting the blood sample on the surface of the skin with the sampling module by extending the capillary tube relative to the lancet;
   wherein the lancing device includes a pusher;
   wherein said collecting the sample of blood includes pushing the capillary tube with the pusher to extend the capillary tube relative to the lancet to minimize the amount of direct manual handling of the capillary tube;
   wherein during said pushing the capillary tube moves from inside the housing to project outside of the housing; and
   wherein the disposable sampling module includes a slot with a plurality of pairs of opposed holding fingers that frictionally grip the capillary tube.

2. The method of claim 1 further comprising transferring the sample module for analysis after the blood sample has been obtained.

3. The method of claim 1, further comprising:
   wherein the pusher includes a knob that is biased by a spring; and
   wherein said pushing the capillary tube includes applying force to the knob.

4. The method of claim 1, wherein said loading the disposable sampling module includes:
   loading the lancet into a carrier; and
   attaching the carrier to the lancing device, wherein the carrier is configured to attach to the lancing device in only one circumferential relationship to ensure the capillary tube is aligned with the pusher.

5. The method of claim 1, further comprising:
   unloading the disposable sampling module from the lancing device;
   discarding the disposable sampling module; and
   loading a new disposable sampling module into the lancing device.

6. A method of sampling comprising:
   loading a disposable sampling module having a lancet and a capillary tube into a lancing device that includes a housing, wherein the capillary tube is located inside the housing during said loading the disposable;
   initiating a lancing cycle by pressing the lancing device against skin;
   lancing the skin to obtain a blood sample in response to said initiating the lancing cycle;
   collecting the blood sample on the surface of the skin with the sampling module by extending the capillary tube relative to the lancet;
   wherein the lancing device includes a pusher;
   wherein said collecting the sample of blood includes pushing the capillary tube with the pusher to extend the capillary tube relative to the lancet, wherein during said pushing the capillary tube moves from inside the housing to project outside of the housing;
   wherein said loading the disposable sampling module includes loading the lancet into a carrier, and
   attaching the carrier to the lancing device, wherein the carrier is configured to attach to the lancing device in only one circumferential relationship to ensure the capillary tube is aligned with the pusher;
   wherein the carrier includes guide ramps;
   wherein the lancet includes bosses;
   wherein said loading the lancet into the carrier includes riding the bosses of the lancet along the guide ramps of the carrier; and
   wherein the disposable sampling module includes a slot with a plurality of pairs of opposed holding fingers that frictionally grip the capillary tube.

7. The method of claim 6, further comprising transferring the sampling module for analysis after the blood sample has been obtained.

8. A method of sampling according to claim 6, further comprising analyzing said blood sample.

9. A method of sampling according to claim 6, further comprising informing a user to remove said skin when said lancing cycle is complete.

10. A method of sampling according to claim 9 wherein informing said user comprises giving a visual signal when said lancing cycle is complete.

11. The method of claim 6, further comprising:
    unloading the disposable sampling module from the lancing device;
    discarding the disposable sampling module; and
    loading a new disposable sampling module into the lancing device.

12. A method of sampling comprising:
    loading a disposable sampling module having a lancet and a capillary tube into a lancing device that includes a housing, wherein the capillary tube is located inside the housing during said loading the disposable;
    initiating a lancing cycle pressing the housing of the lancing device against skin;
    lancing the skin to obtain a blood sample in response to said initiating the lancing cycle;
    collecting the blood sample on the surface of the skin with the sampling module by extending the capillary tube relative to the lancet;
    wherein the lancing device includes a pusher;
    wherein said collecting the sample of blood includes pushing the capillary tube with the pusher to extend the capillary tube relative to the lancet to minimize the amount of direct manual handling of the capillary tube;
    wherein the disposable sampling module includes a slot with a plurality of pairs of opposed holding fingers that frictionally grip the capillary tube; and
    wherein during said pushing the capillary tube moves from inside the housing to project outside of the housing;
    wherein said loading the disposable sampling module includes:
    loading the lancet into a carrier; and
    attaching the carrier to the lancing device, wherein the carrier is configured to attach to the lancing device in only one circumferential relationship to ensure the capillary tube is aligned with the pusher;

wherein the disposable sampling module includes a cylindrical body, a needle projecting from a lower end of the body, a lower boss projecting radially outward from the body, and a pair of upper bosses projecting radially outward from the body;

wherein the lower boss and the upper bosses are circumferentially spaced apart from one another;

wherein the upper bosses are disposed at a same elevation above the lower boss;

wherein the carrier has an inner surface that includes a pair of downwardly inclined, upwardly facing guide ramps;

wherein the guide ramps have lower ends that intersect to form an upwardly open recess; and wherein said loading the lancet into the carrier includes
engaging the guide ramps with the upper bosses of the disposable sampling module, and
ensuring the lower boss enters the recess in the carrier by guiding the upper bosses with the guide ramps.

13. The method of claim 12, wherein the disposable sampling module includes a slot with a plurality of pairs of opposed holding fingers that frictionally grip the capillary tube.

14. The method of claim 13, wherein the needle and the capillary are offset from one another in a parallel relationship.

* * * * *